US012427182B2

(12) United States Patent
Hamed

(10) Patent No.: US 12,427,182 B2
(45) Date of Patent: *Sep. 30, 2025

(54) TOPICAL ERYTHROPOIETIN FORMULATIONS AND METHODS FOR IMPROVING WOUND HEALING WITH AND COSMETIC USE OF THE FORMULATIONS

(71) Applicant: Remedor Biomed Ltd., Nazareth Illit (IL)

(72) Inventor: Saher Hamed, Nazareth Illit (IL)

(73) Assignee: REMEDOR BIOMED LTD., Nazareth Illit (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/537,020

(22) Filed: Nov. 29, 2021

(65) Prior Publication Data

US 2022/0339252 A1   Oct. 27, 2022

Related U.S. Application Data

(63) Continuation of application No. 15/757,186, filed as application No. PCT/IB2016/055247 on Sep. 1, 2016, now Pat. No. 11,213,569.

(60) Provisional application No. 62/214,618, filed on Sep. 4, 2015.

(51) Int. Cl.
| | |
|---|---|
| *A61K 38/00* | (2006.01) |
| *A61K 8/04* | (2006.01) |
| *A61K 8/64* | (2006.01) |
| *A61K 9/00* | (2006.01) |
| *A61K 9/06* | (2006.01) |
| *A61K 38/18* | (2006.01) |
| *A61K 38/39* | (2006.01) |
| *A61K 47/10* | (2017.01) |
| *A61K 47/14* | (2017.01) |
| *A61K 47/18* | (2017.01) |
| *A61K 47/32* | (2006.01) |
| *A61P 17/02* | (2006.01) |
| *A61Q 19/00* | (2006.01) |
| *C07K 14/505* | (2006.01) |
| *C07K 14/78* | (2006.01) |
| *C07K 14/00* | (2006.01) |

(52) U.S. Cl.
CPC .......... *A61K 38/1816* (2013.01); *A61K 8/042* (2013.01); *A61K 8/64* (2013.01); *A61K 9/0014* (2013.01); *A61K 9/06* (2013.01); *A61K 38/39* (2013.01); *A61K 47/10* (2013.01); *A61K 47/14* (2013.01); *A61K 47/18* (2013.01); *A61K 47/32* (2013.01); *A61P 17/02* (2018.01); *A61Q 19/00* (2013.01); *A61K 2300/00* (2013.01); *C07K 14/00* (2013.01)

(58) Field of Classification Search
None
See application file for complete search history.

(56) References Cited

U.S. PATENT DOCUMENTS

| | | |
|---|---|---|
| 4,851,434 A | 7/1989 | Deckner |
| 5,821,220 A | 10/1998 | Beaulieu et al. |
| 5,877,149 A | 3/1999 | Beaulieu et al. |
| 2006/0182789 A1 | 8/2006 | Ameri et al. |
| 2008/0187591 A1 | 8/2008 | Rhee et al. |
| 2009/0022683 A1 | 1/2009 | Song et al. |
| 2009/0311240 A1 | 12/2009 | Mittermayr et al. |
| 2010/0172848 A1 | 7/2010 | Modak et al. |
| 2010/0278916 A1 | 11/2010 | Bader |
| 2011/0189140 A1 | 8/2011 | Christman et al. |
| 2014/0154205 A1 | 6/2014 | Hamed |

FOREIGN PATENT DOCUMENTS

| | | | |
|---|---|---|---|
| JP | H11246420 A | 9/1999 | |
| JP | 2006104466 A | 4/2006 | |
| JP | 2010536745 A | 12/2010 | |
| KR | 20050016305 A | 2/2005 | |
| WO | WO-2008079898 A1 * | 7/2008 | ............. A61K 31/74 |

OTHER PUBLICATIONS

Liu et al. Influence of cyclosporin A eye drops on aquaporin protein 3 expression in corneal epithelial injury. Abstract. International Journal of Ophthalmology, vol. 10, No. 3, pp. 430-431 (Mar. 2010). (Year: 2010).*
Hamed et al. Topical erythropoietin improves burn wound healing and the skin's mechanical properties through an aquaporin-3-dependent mechanism in diabetic pigs: An effect potentiated by fibronectin. Wound Repair and Regeneration, vol. 20, No. 5, Abstract. pp. A109 (Sep.-Oct. 2012). (Year: 2012).*
Hung, C. 18b-glycyrrhetinic derivative induces the expression of aquaporin-3 in keratinocytes and fibroblasts. Journal of Dermatological Science, vol. 60, No. 3, pp. e24. Abstract No. P07-35 (Dec. 2010). (Year: 2010).*
Bollag et al. Regulation of aquaporin-3 levels in epidermal keratinocytes through histone deacetylase inhibition. Journal of Investigative Dermatology, vol. 135, Supp. SUPPL. 1,pp. S69. Abstract. Number: 403 (May 2015). (Year: 2015).*
Roberts, et al.: "Physical changes in dermal tissues around chronic venous ulcers", Proceedings of the 7th European Conference on Advances in Wound Management, Nov. 18-20, 1997; Harrogate, UK, J. European Wound Management Association, 1998:104-105.
Tsukada, et al.: "The pH Changes of Pressure Ulcers Related to the Healing Process of Wounds", J. Wounds (1992), 4(1):16-20.

(Continued)

*Primary Examiner* — Elizabeth C. Kemmerer
*Assistant Examiner* — Regina M DeBerry
(74) *Attorney, Agent, or Firm* — NORTON ROSE FULBRIGHT US LLP

(57) ABSTRACT

Topical formulations containing erythropoietin (EPO), and also preferably fibronectin (FN), especially gel formulations, are used to accelerate wound healing, e.g., from a burn, compared to the healing process without such a formulation being applied.

5 Claims, 14 Drawing Sheets

(56) References Cited

OTHER PUBLICATIONS

Hamed, et al.: "Topical Erythropoietin Treatment Accelerates the Healing of Cutaneous Burn Wounds in Diabetic Pigs Through an Aqauaporin-3-Dependent Mechanism", DOI: 10.2337/db16-1205, (2017), pp. 1-21, https:/diabetesjournals.org/node/79378.

Bodo, et al.: "Human hair follices are an extrarenal source and a nonheatopoietic target of erythropoietin", The FASEB Journal, (21), (2007), pp. 3346-3348.

Row, et al.: "Handbook of Pharmaceutical Excipients", Fifth Edition. Libros Digitales-Pharmaceutical Press, (2009), pp. 1-918; https://www.academia.edu/33834163/Handbook_of_Pharmaceutical_Excipients_Fifth_Edition.

Agre, et al.: "The Aqyuaporins, Blueprints for Cellular Plumbing Systems", J. Biol. Chem., 273(24), (1998), pp. 14659-14662.

Anagnostou, et al.: "Erythropoietin has a mitogenic and positive chemotactic effect on endothelial cells", Proc. Natl. Acad. Sci., 87 (1990), pp. 5978-5982.

Brown, et al.: "Expression of Vascular Permeability Factor (Vascular Endothelial Growth Factor by Epidermal Keratinocytes during Wound Healing", J. Exp. Med. 176 (1992) (http://doi.org/10.1084/jem.176.5.1375), pp. 1375-1379.

Davis, et al.: "Second-Degree Burn Healing: The Effect of Occlusive Dressings and a Cream", J. Sergical Reserach 48 (1990), pp. 245-248.

Gong, et al.: "EPO and a-MSH prevent ischemia/reperfusion-induced down-regulation of AQPs and sodium transporters in rat kidney", Kidney International, 66(2004), pp. 683-695.

Hamed, et al.: "Topical Erythropoietin Promotes Wound Repair in Diabetic Rats", www.jidonline.org, The Society for Investigative Dermatology (2009), pp. 1-8.

Hamed, et al.: "Fibronectin Potentiates Topical Erythropoietin-Induced Wound Repair in Diabetic Mice", www.idonline.org, The Society for Investigative Dermatology (2011), pp. 1-10.

Hamed, et al.: "Erythropoietin, a novel repurposed drug: An Innovative treatment for wound healing in patients with diabetes mellitus", Wound Rep. Reg. 22 (2013), pp. 23-33.

Hara, et al.: "Safe Induction of Diabetes by High-Dose Streptozotocin in Pigs", Pancreas, 36(1), (2008), pp. 31-38.

Hara-Chikuma, et al.: "Aquaporin-3 functions as a glycerol transporter in mammalian skin", Biol. Cell 97 (2005), pp. 479-486.

Hara-Chikuma, et al.: "Physiological roles of glycerol-transporting aquaporins: the aquaglyceroporins", Cell. Mol. Life Sci. 63 (2006), pp. 1386-1392.

Hara-Chikuma, et al.: "Aquaporin-3 facilitates epidermal cell migration and proliferation during wound healing", J. Mol. Med. 86 (2008), pp. 221-231.

Hara-Chikuma, et al.: "Roles of Aquaporin-3 in the Epidermis", The Society for Investigative Dermatology, J. Invest Dermatol. Sep. 2008; 128(9): 2145-51(2008).

Hehenberger, et al.: "Impaired proliferation and increased L-lactate production of dermal fibroblasts in the GK-rat, a spontaneous model of non-insulin dependent diabetes mellitus", Wound Repair Regen. Mar.-Apr. 1998; 6(2): 135-41 (1998).

Levin, et al.: "Aquaporin-3-Dependent Cell Migration and Proliferation during Corneal Re-epithelialization", IOVS, 47 (10), (2006), pp. 4365-4372.

Mansbridge, et al.: "Growth factors secreted by fibroblasts: role in healing diabetic foot ulcers", Diabetes, Obesity and Metabolism 1 (1999), pp. 265-279.

Martin, Paul :"Wound Healing—Aiming for Perfect Skin Regeneration", Science 276 (1997), pp. 75-81.

Mustoe, Thomas: "Understanding chronic wounds: a unifying hypothesis on their pahtogenesis and implications for therapy", Am. J. Surg. 187 (2004), pp. 65S-70S.

Sebastian, et al.: "Epidermal aquaporin-3 is increased in the cutaneous burn wound", Burns 41(4), (2015), pp. 843-847.

Sen, et al.: "Human skin wounds: A major and snowballing threat to public health and the economy", Wound Rep. Reg. 17 (2009), pp. 763-771.

Sheetz, et al.: "Molecular Understanding of Hyperglycemia's Adverse Effects for Diabetic Complications", JAMA 288 (20), (2002), pp. 2579-2588.

Shukla, et al.: "Differential Expression of Proteins during Healing of Cutaneous Wounds in Experimental Normal and Chronic Models", Biochem. Biophys. REs. Comm. 244(2), (1998), pp. 434-439.

Stadelmann, et al.: "Physiology and Healing Dynamics of Chronic Cutaneous Wounds", Am. J. Surg. 176 (Suppl. 2A), (1998), pp. 27S-38S.

Sugimoto, et al.: "Impaired Aquaporin 3 Expression in Reepithelialization of Cutaneous Wound Healing in the Diabetic Rat", Biol. Res. for Nursing 15(3), (2012), pp. 347-355.

Sullivan, et al.: "The pig as a model for human wound healing", Wound Rep. Reg. 9(2), (2001), pp. 66-76.

Tentolouris, et al.: "Moisture Status of the Skin of the Feet Assessed by the Visual Test Neuropad Correlates With Foot Ulceration in Diabetes", Diabetes Care 33(5), (2010), pp. 1112-1114.

Vedrenne, et al.: "The complex dialogue between (myo)fibroblasts and the extracellular matrix during skin repair processes and ageing", Pathologie Biologie 60 (2012), pp. 20-27.

Winter, George D.: "Formation of the Scab and the Rate of Epithelization of Superficial Wounds in the Skin of the Young Domestic Pig", Nature 193 (1962), pp. 293-294.

Japan Pharmaceutical Excipients Council, Excipient Encyclopedia (2007), Yakuji Nippo, Ltd., pp. 65, 82-83, 194, 215-216, and 249 (with electronic translation into English).

Choukse, et al.: "Formulation and Evaluation of Pluronic lecithin organogel of Flurbiprofen," Journal of Biomedical and Pharmaceutical Research, 1(1), 2012, pp. 1-7.

Chung, et al.: "The Reduction of Azo Dyes by the Intestinal Microflora," Critical Reviews in Microbiolology, 18(3):175-190, (1992).

Garje and Salunkhe: "Review on: Anti-Inflammatory Herbal Gel of Boswellia Serrata & Vitex Negundo," Int'l Journal of Pharma and Bio Sciences (IJPBS), vol. 3, Issue 2, (2012), pp. 41-49.

Gethin, Georgina: "The significance of surface pH in chronic wounds," J. Wounds UK, 3(3):52-56, (2007).

Gupta, et al.: "Organogel: A Viable Alternative for Existing Carrier System," Int'l Journal of Comprehensive Pharmacy, 2(5):1-5, (2011). (Abstract).

Hoffman, et al.: "The use of proteases as prognostic markers for the healing of venous leg ulcers," J. Wound Care, 3(6):273-276, (1999).

Jensen, et al.: "Review: efficacy of alginate supplementation in relation to appetite regulation and metabolic risk factors: evidence from animal and human studies," Obesity Reviews, 14(2):129-144, (2013).

Leveen, et al.: 'Chemical Acidification of Wounds. An Adjuvant to Healing and the Unfavorable Action of Alkalinity and Ammonia,' J. Ann Surg. 178(6):745-753, (1973).

Marto, et al.: "Starch-based Pickering emulsions for topical drug delivery: a QbD approach," Colloids and Surfaces B: Biointerfaces, 135:183-192, (2015).

Ovington, Liza G.: "Asdvances in wound dressings," J. Clinics in Dermatology, 25:33-38, (2007).

Prabha, et al.: "Comparative Invitro Release of Diclofenac Sodium Gel From Different Marketed Products," Int'l Journal of Life Science & Pharma Research, 2(3):88-93, (2012).

Kaur, et al.: "Topical Gel: A Recent Approach for Novel Drug delivery," Asian Journal of Biomedical and Pharmaceutical Sciences, 3(17):1-5, (2013).

Schneider, et al.: "Influence of pH on wound healing: a new perspective for wound-therapy?", Arch. Dermatol. Res. 298(9):413-420, (2007).

Schweizer, et al.: "Controlled release of therapeutic antibody formats,". Eur. J. Pharm. Biopharm (EJPB), 88(2):291-309, (2014).

Sheikh, et al.: "Formulation development and characterization of aceclofenac gel containing linseed oil and ginger oleoresin," Int'l J. PharmTech. Res, (IJPTR) Coden USA 3(3):1448-1453, ( 2011).

(56) References Cited

OTHER PUBLICATIONS

Shin, et al.: "Accuracy of Root ZX in teeth with simulated root perforation in the presence of gel or liquid type endodontic irrigant," Restorative Dentistry & Endodontics, (RDE), 37(3):149-154, (2012).
Uche, Don Okpala V.: "Sol-gel technique: A veritable tool for crystal growth," Advances in Applied Science Research, (AASRFS) 4(1):506-510, (2013).
Al-Khashab, et al.: "Formulation and evaluation of ciprofloxacin as a topical gel," Asian Journal of Pharmaceutical Sciences, (AJPS), 8(2):80-95, (2010).
USP 41. Unites States Pharmacopeia. 41st Ed., The United States Pharmacopeial Convention; NF 36 The National Formulary, vol. 4, Biological Tests, pp. 6061-6063, (2018).
Ferry, John D.: "Viscoelastic Properties of Polymers," 3rd Ed., John Wiley and Sons, New York, (1980), pp. 529-530.
The European Pharmacopoeia. 8th Ed. vol. 1. Strasbourg Cedex: Council of Europe; (2013), pp. 2162-2166.

\* cited by examiner

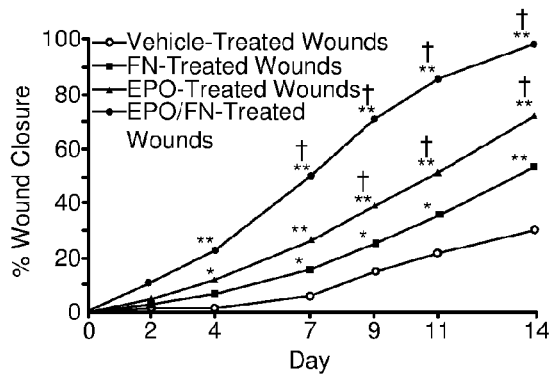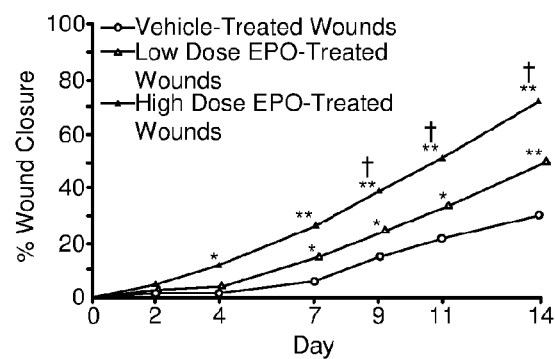
FIG. 1A  FIG. 1B
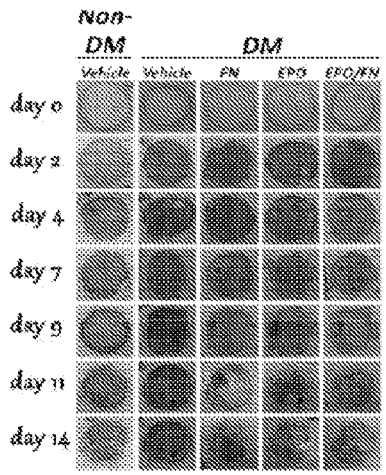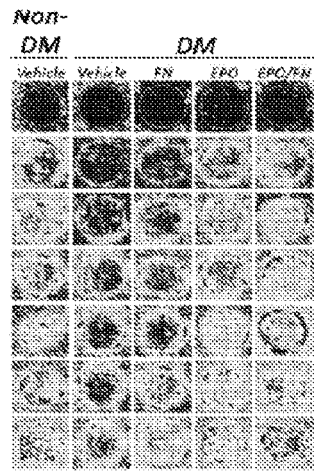
FIG. 1C
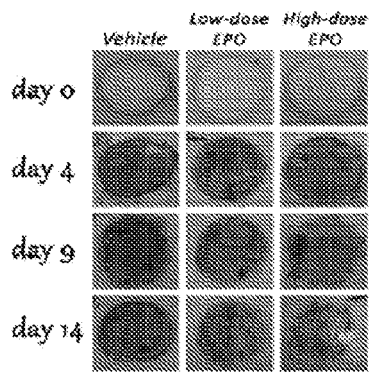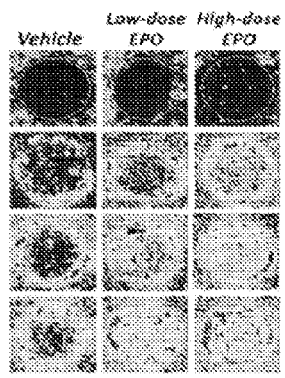
FIG. 1D

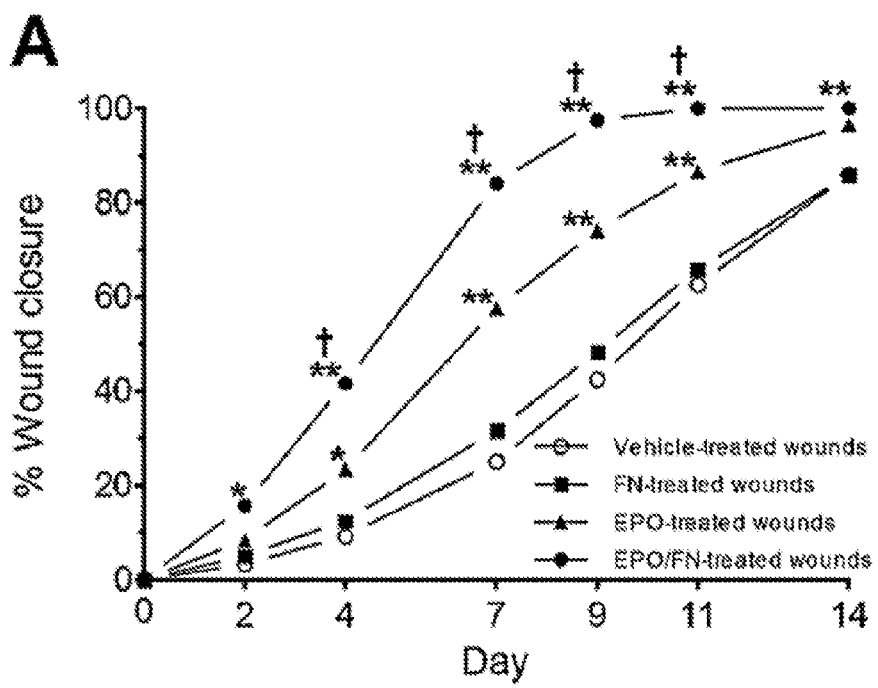
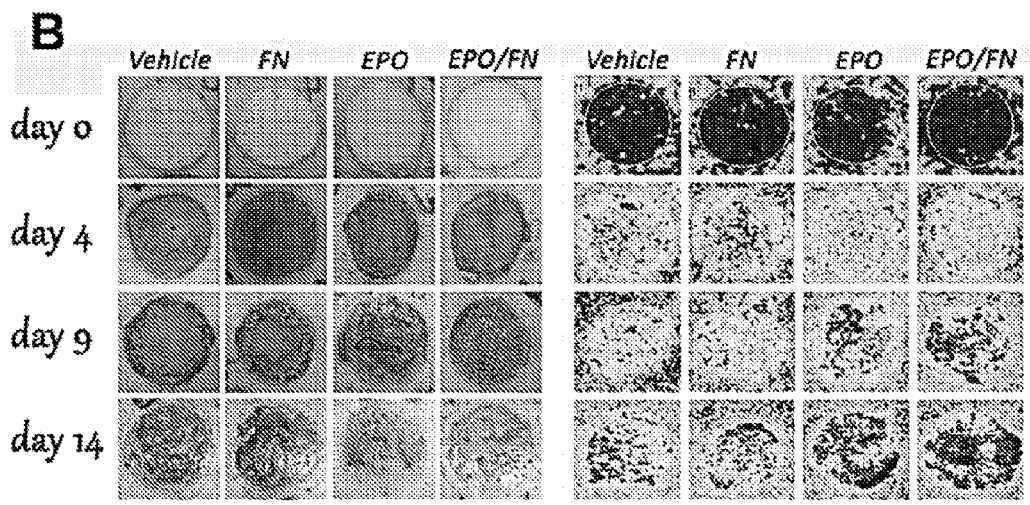
FIG. 2A-B

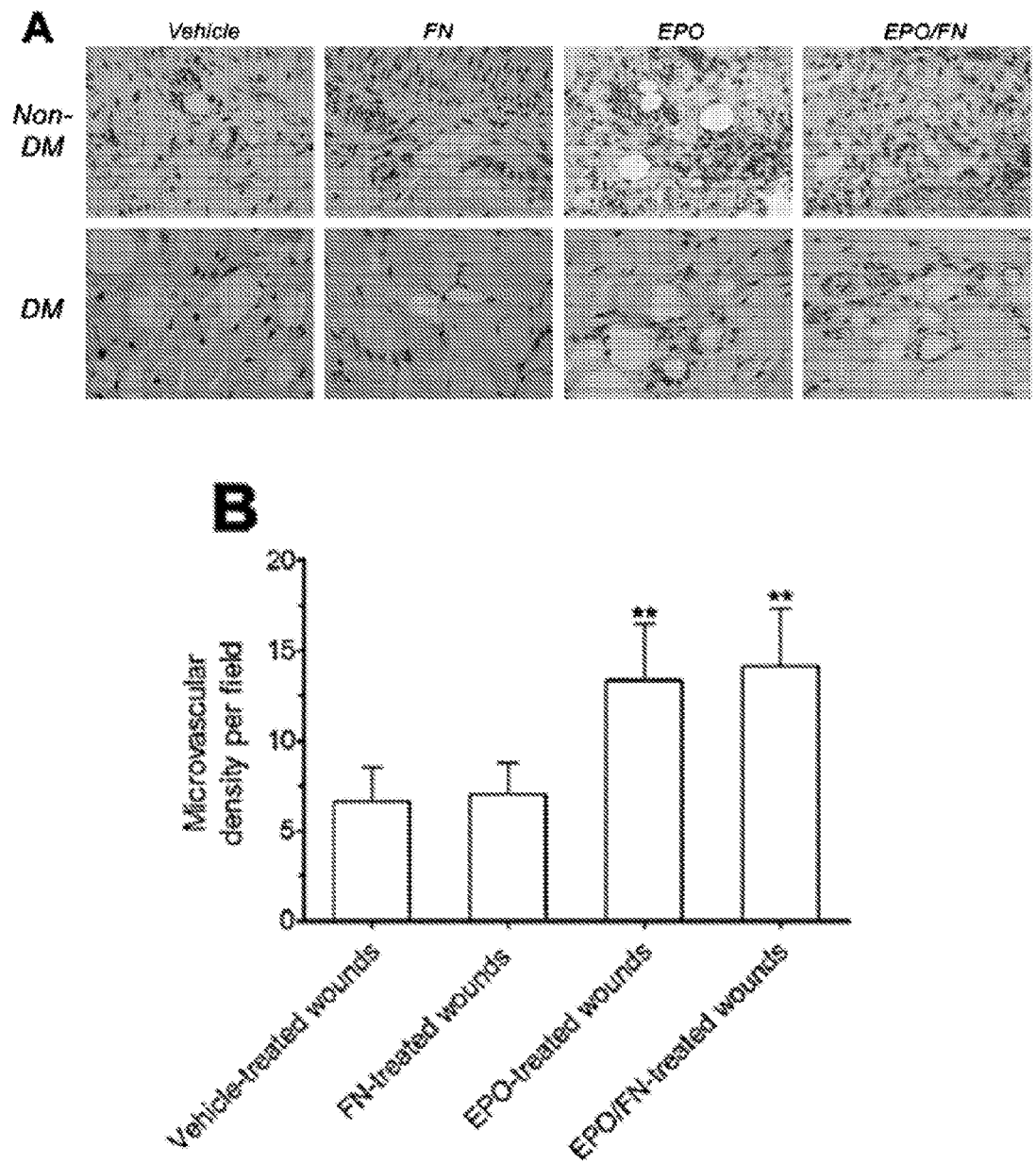
FIG. 3A-B

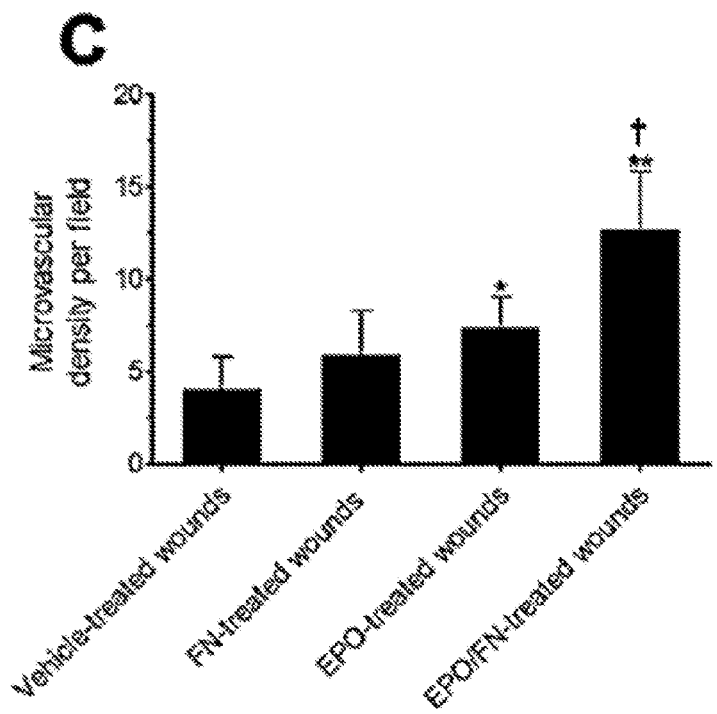
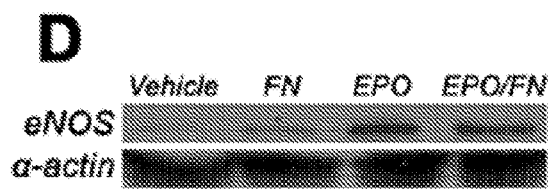
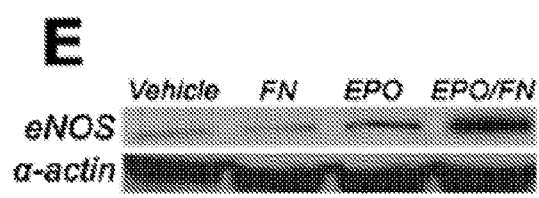
FIG. 3C-E

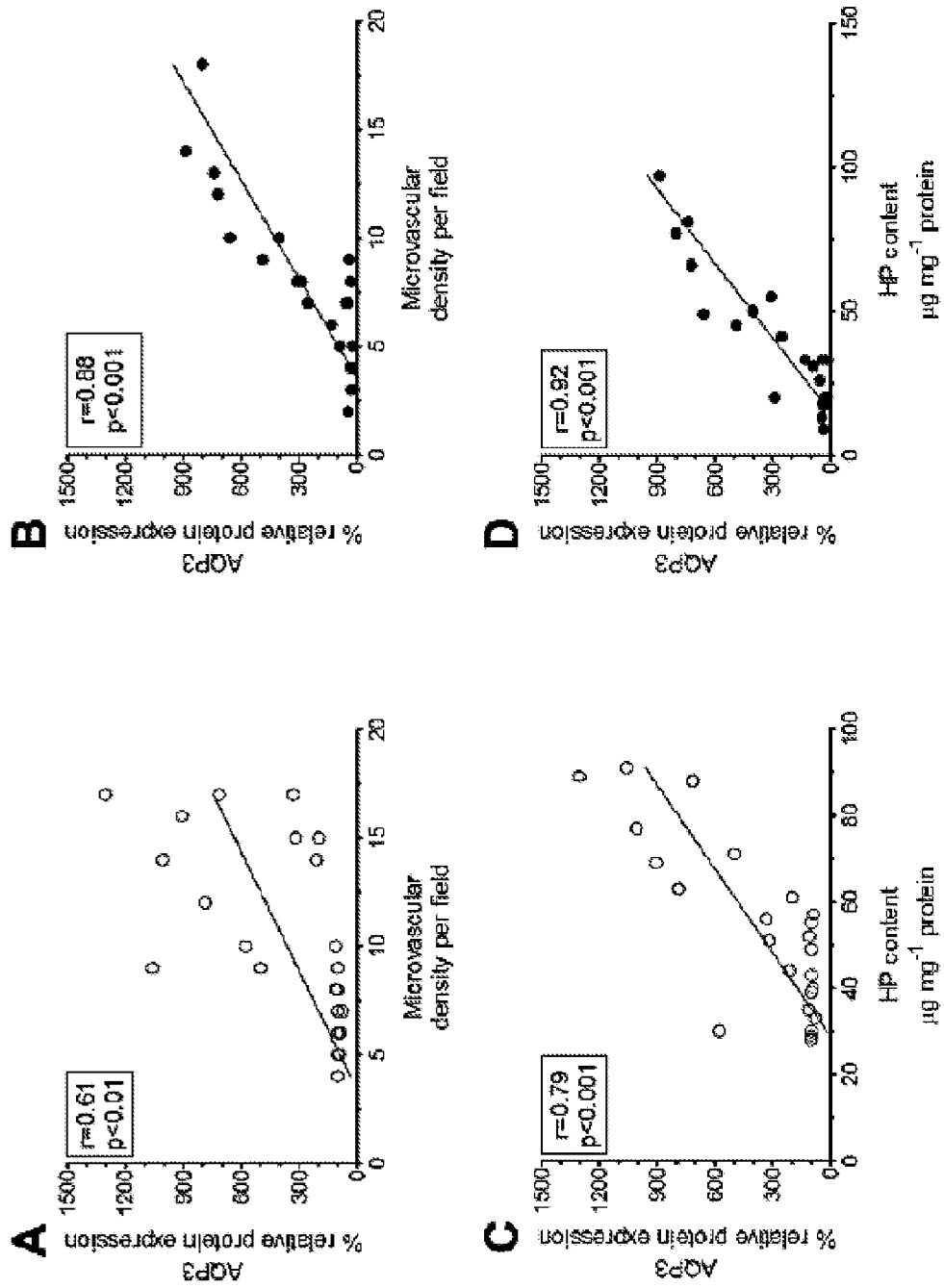
FIG. 7A-D

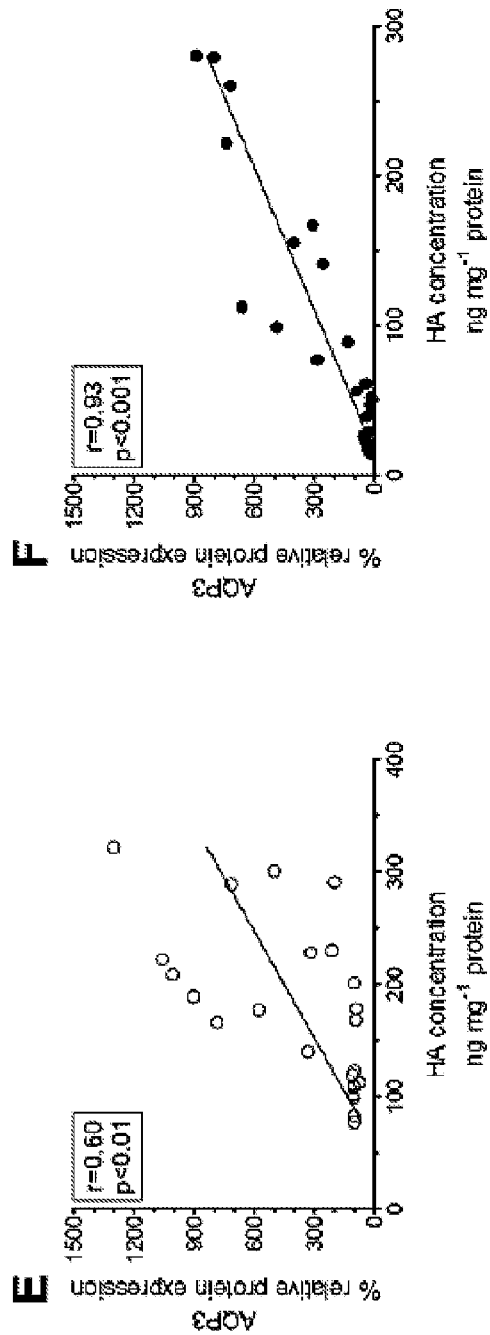
FIG. 7E-F

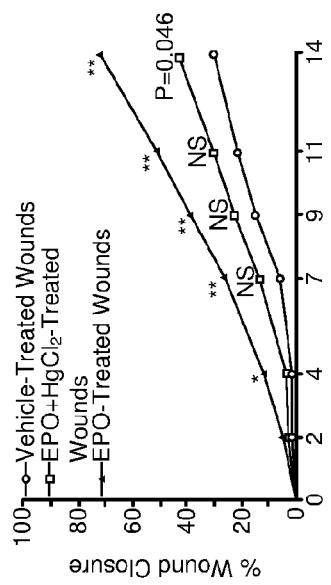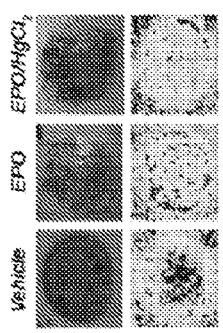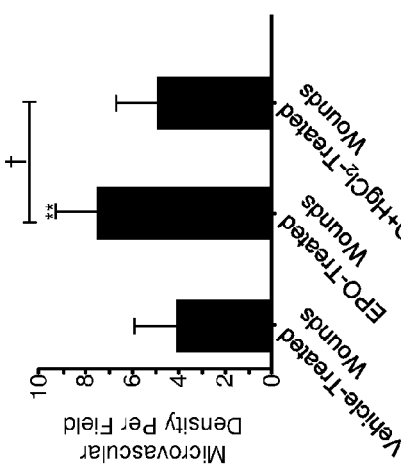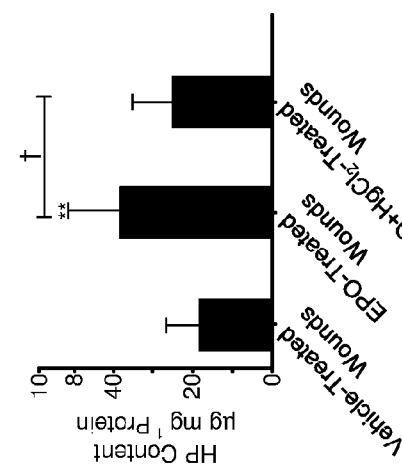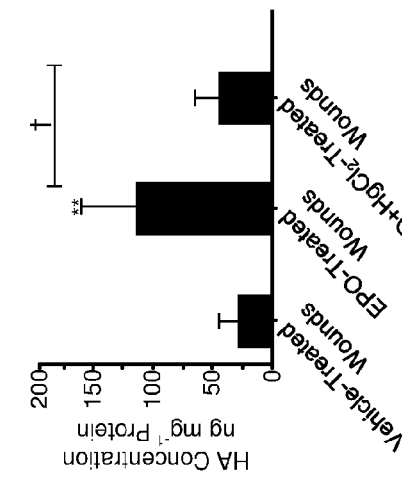
FIG. 8A, FIG. 8B, FIG. 8C, FIG. 8D, FIG. 8E, FIG. 8F

TOPICAL ERYTHROPOIETIN FORMULATIONS AND METHODS FOR IMPROVING WOUND HEALING WITH AND COSMETIC USE OF THE FORMULATIONS

This application is a continuation patent application of U.S. patent application Ser. No. 15/757,186 filed Mar. 2, 2018, which is a 371 of International Patent Application No. PCT/IB2016/055247 filed Sep. 1, 2016, which claims the benefit of priority from U.S. Provisional Patent Application Ser. No. 62/214,618 filed Sep. 4, 2015, the contents of each of which is hereby incorporated by reference in its entirety.

BACKGROUND OF THE INVENTION

1. Field of the Invention

The present invention relates to topical formulations containing erythropoietin (EPO), and also preferably fibronectin (FN), especially gel formulations. The present invention also relates to use of these topical formulations to accelerate wound healing, e.g., from a burn, compared to the healing process without such a formulation being applied. Methods of preparing the formulations are also a part of the present invention.

2. Description of Related Art

According to the United States Centers for Disease Control and Prevention (CDC), more than 380 million people worldwide suffer from diabetes mellitus (DM). The CDC also estimates that 5% of these individuals will develop a diabetic skin ulcer (DSU) and that 1% will require a lower-extremity amputation. Despite many advances in wound care and management (Sen, 2009), wound healing in DM is delayed because all phases of the orchestrated cascade of cellular and biochemical events of wound healing are disrupted (Brown, 1992; Shukla, 1998; Mustoe, 2004). Additionally, the healing of a DSU is delayed because of impaired angiogenesis, insufficient blood flow, increased inflammation, diminished proliferation of fibroblasts (Hehenberger, 1999), and reduced reepithelialization by keratinocytes (Mansbridge, 1999; Stadelmann, 1998; Sheetz, 2002).

The glycoprotein hormone, erythropoietin (EPO), regulates red blood cell mass, and is an approved drug for treating anemia. EPO also has nonhematopoietic targets in the skin, and it has been shown that these targets participate in the healing of skin wounds (Hamed, 2014). It has been previously reported that the healing of cutaneous wounds in rats and mice with experimentally-induced DM is accelerated following the topical application of recombinant human EPO to the cutaneous wounds by (a) stimulating angiogenesis, reepithelialization, and collagen deposition, and (b) suppressing the inflammatory response and apoptosis (Hamed, 2010). The beneficial actions of EPO on wound healing in DM are complemented by fibronectin (FN). FN facilitates the formation of the provisional wound matrix and prevents its dissociation (Hamed, 2011).

Aquaporins (AQP) are integral membrane proteins whose function is to regulate intracellular fluid hemostasis by enabling the transport of water and glycerol. AQPs are expressed in the plasma membranes of keratinocytes in the basal layer of the skin and the medullary collecting ducts of the kidney (Agre 1998). Downregulated expression of AQPs may be the cause of the reduction in urinary-concentrating ability in acute renal failure and EPO can prevent this downregulation (Gong, 2004). AQP3 is the AQP that is expressed in the skin (Hara-Chikuma, 2005) where it facilitates cell migration and proliferation and reepithelialization during wound healing (Hara-Chikuma 2006, Levin, 2006, Hara-Chikuma, 2008). A positive role for moisture in healing skin wounds was first shown in 1962, when Winter investigated scab formation and the rate of epithelialization of superficial wounds in pig skin and reported that moist wounds heal faster than dry ones (Winter, 1962). As a corollary, dryness of the skin of the feet correlates with foot ulceration in patients with DM (Tentolouris, 2010). A specific role for AQP3 in diabetic wound healing was posited when it was found that AQP3 is downregulated in the regenerating epidermis during the healing of full-thickness cutaneous wounds in rats with DM (Sugimoto, 2012). The work indicated that EPO could be used to stimulate the healing of non-healing wounds. Such findings also suggest the existence of a causal relationship between impaired AQP3 expression and delayed reepithelialization in DM, which involves (a) impaired movement and proliferation of those cells that participate in angiogenesis, (b) reduced production of the extracellular matrix (ECM) by fibroblasts, and (c) failure of keratinocytes to reepithelialize a cutaneous skin wound.

SUMMARY OF THE INVENTION

The present invention relates to topical formulations containing erythropoietin (EPO), and also preferably fibronectin (FN), especially gel formulations. In some embodiments a pharmaceutical composition is described comprising a gel, erythropoietin and fibronectin. In some aspects, the fibronectin is present in the composition in an amount potentiates the salutary actions of the erythropoietin when applied to a wound. In other aspects, a method of treating a wound comprising topically applying a therapeutically effective amount of a pharmaceutical composition comprising a gel, erythropoietin and fibronectin wherein the fibronectin is present in the composition in an amount potentiates the salutary actions of the erythropoietin when applied to a wound to a wound in order to treat the wound, is described. In some embodiments, the wound is a wound of a subject diagnosed or is suspected of having high blood sugar. In other embodiments, the wound is a wound of a subject diagnosed or is suspected of having insulin resistance. In yet other embodiments, the wound is a wound of a subject diagnosed or is suspected of having a deficit in insulin production or is insulin resistant. In further embodiments, the wound is a wound of a subject that is diagnosed as or suspected of being diabetic. In specific aspects, the wound is a wound of a human subject.

The gel formulation preferably contains at least one member from the non-limiting list of excipients including, e.g., benzyl alcohol, glycerol or other alcohols, polymers such as a polyvinyl carboxy polymer such as Carbomer 940 which may be used as, e.g., a viscosity enhancer, gelling agent, or suspension agent (Carbomer 940 is cross linked with ethers of pentaerythritol), parabens such as methylparaben, propylparaben; triethanolamine, and other excipients known in the art for making gels, and any combination thereof. The gel formulations of the invention should also include water.

In certain aspects of a pharmaceutical composition comprising a gel, erythropoietin and fibronectin the erythropoietin is present at a concentration of 5% w/w by weight of the composition. In other aspects, the fibronectin is present at a concentration of 30% w/w. In still other aspects, the composition comprises erythropoietin at a concentration of between 0.01% to 30% (w/w) and fibronectin at a concentration of between 0.01% to 50% (w/w). In other embodiments, the composition comprises erythropoietin at a concentration of between 0.01% to 30% (w/w) and fibronectin at a concentration of between 0.01% to 50% (w/w), glycerol at a concentration of between 0.01% to 30% (w/w), Carbomer 940 at a concentration of between 0.01% to 30% (w/w), benzyl alcohol at a concentration of between 0.01% to 30% (w/w), triethanolamine at a concentration of between 0.01% to 30% (w/w), methylparaben at a concentration of between 0.01% to 30% (w/w), propylparaben at a concentration of between 0.01% to 30% (w/w). In yet further aspects, the composition comprises glycerol at 5% (w/w), Carbomer 940 at 1% (w/w), benzyl alcohol at 2% (w/w), triethanolamine at 0.9% (w/w), methylparaben at 0.2% (w/w), propylparaben at 0.05% (w/w). In specific aspects, the composition comprises glycerol at 5% (w/w), Carbomer 940 at 1% (w/w), benzyl alcohol at 2% (w/w), triethanolamine at 0.9% (w/w), methylparaben at 0.2% (w/w), propylparaben at 0.05% (w/w) and water to 100% (w/w). In some embodiments, the gel is a fibrin, collagen or hyaluronic acid gel. In other embodiments, the gel comprises fibrin, collagen or hyaluronic acid. In particular embodiments, the gel is a hydrogel.

In certain aspects a pharmaceutical composition comprising erythropoietin, wherein the composition is formulated as a gel, is described. In specific embodiments, the composition comprises fibronectin. In still other embodiments, the erythropoietin is present at a concentration of 5% w/w. In yet other embodiments, the fibronectin is present at a concentration of 30% w/w. In other aspects, the composition comprises erythropoietin at a concentration of between 0.01% to 30% (w/w), fibronectin at a concentration of between 0.01% to 50% (w/w), glycerol at a concentration of between 0.01% to 30% (w/w), Carbomer 940 at a concentration of between 0.01% to 30% (w/w), benzyl alcohol at a concentration of between 0.01% to 30% (w/w), triethanolamine at a concentration of between 0.01% to 30% (w/w), methylparaben at a concentration of between 0.01% to 30% (w/w), propylparaben at a concentration of between 0.01% to 30% (w/w). In still other aspects, the composition comprises glycerol at 5% (w/w), Carbomer 940 at 1% (w/w), benzyl alcohol at 2% (w/w), triethanolamine at 0.9% (w/w), methylparaben at 0.2% (w/w), propylparaben at 0.05% (w/w). In yet other embodiments, composition comprises glycerol at 5% (w/w), Carbomer 940 at 1% (w/w), benzyl alcohol at 2% (w/w), triethanolamine at 0.9% (w/w), methylparaben at 0.2% (w/w), propylparaben at 0.05% (w/w) and water to 100% (w/w). In certain aspects, the gel is a fibrin, collagen or hyaluronic acid gel. In other aspects, the gel comprises fibrin, collagen or hyaluronic acid. In some embodiments, the gel is a hydrogel.

Also provided is a method of treating a wound in a subject comprising administering to the subject a therapeutically effective amount of a composition comprising erythropoietin, wherein the composition is a gel. In certain embodiments, the composition comprises fibronectin. In other embodiments, the erythropoietin is present at a concentration of 5% w/w. In some other embodiments, the fibronectin is present at a concentration of 30% w/w. In still other embodiments, the composition comprises erythropoietin at a concentration of between 0.01% to 30% (w/w), fibronectin at a concentration of between 0.01% to 50% (w/w), glycerol at a concentration of between 0.01% to 30% (w/w), Carbomer 940 at a concentration of between 0.01% to 30% (w/w), benzyl alcohol at a concentration of between 0.01% to 30% (w/w), triethanolamine at a concentration of between 0.01% to 30% (w/w), methylparaben at a concentration of between 0.01% to 30% (w/w), propylparaben at a concentration of between 0.01% to 30% (w/w). In other specific embodiments, the composition comprises glycerol at 5% (w/w), Carbomer 940 at 1% (w/w), benzyl alcohol at 2% (w/w), triethanolamine at 0.9% (w/w), methylparaben at 0.2% (w/w), propylparaben at 0.05% (w/w). In still other embodiments, the composition comprises glycerol at 5% (w/w), Carbomer 940 at 1% (w/w), benzyl alcohol at 2% (w/w), triethanolamine at 0.9% (w/w), methylparaben at 0.2% (w/w), propylparaben at 0.05% (w/w) and water to 100% (w/w). In yet other aspects, the gel is a fibrin, collagen or hyaluronic acid gel. In other aspects still, the gel comprises fibrin, collagen or hyaluronic acid. In specific aspects, the gel is a hydrogel.

In some aspects, a method of treating a wound in a subject comprising administering to the subject a therapeutically effective amount of a composition comprising erythropoietin, wherein the composition is a gel is provided wherein the subject is diagnosed or is suspected of having high blood sugar. In other aspects, the subject is diagnosed or is suspected of having insulin resistance. In further aspects, the subject is diagnosed or is suspected of having a deficit in insulin production. In further aspects still, the subject is diagnosed as or suspected of being diabetic. In some embodiments, the subject is a human subject. In other embodiments, the composition is provided over multiple administrations. In specific aspects, the composition is administered 2, 3, 4, 5, 6, 7, 8, 9, 10, 11, 12, 13, 14, 15, 16, 17, 18, 19, 20 or more times. In additional aspects, the composition is provided over 1, 2, 3, 4, 5, 6, 7, 8, 9, 10, 11, 12, 13, 14, 15, 16, 17, 18, 19, 21, 22, 23 or 24 weeks. In yet further embodiments, the composition is provided over 1, 2, 3, 4, 5, 6, 7, 8, 9, 10, 11, 12, 13, 14, 15, 16, 17, 18, 19, 21, 22, 23 or 24 months. In additional embodiments, the time interval between administrations is 1, 2, 3, 4, 5, 6, 7, 8, 9, 10, 11, 12, 13 or 14 days. In yet other embodiments, the time interval between administrations is 1, 2, 3, 4, 5, 6, 7 or 8 weeks. In additional embodiments, the gel is formulated for cutaneous administration or is administered cutaneously. In still other embodiments, the wound is an ulcer or a burn. In some other aspects, the wound is a diabetic ulcer. In additional embodiments, the wound is a chronic diabetic ulcer. In some embodiments, the wound is a chronic diabetic ulcer of the extremities. In further aspects still, the wound is a chronic diabetic foot ulcer.

Also provided are methods of treating a wound in a subject comprising administering to the subject a therapeutically effective amount of a composition that induces aquaporin expression. In particular embodiments, the aquaporin is aquaporin-3. In some aspects, the composition is a fibrin, collagen or hyaluronic acid gel. In yet other embodiments, the gel comprises fibrin, collagen or hyaluronic acid. In still other embodiments, the gel is a hydrogel. In particular embodiments, the subject is diagnosed or is suspected of having high blood sugar. In other aspects, the subject is diagnosed or is suspected of having insulin resistance. In further aspects, the subject is diagnosed or is suspected of having a deficit in insulin production. In further aspects still, the subject is diagnosed as or suspected of being diabetic. In some embodiments, the subject is a human subject. In other embodiments, the composition is provided over multiple administrations. In specific aspects, the composition is administered 2, 3, 4, 5, 6, 7, 8, 9, 10, 11, 12, 13, 14, 15, 16, 17, 18, 19, 20 or more times. In additional aspects, the composition is provided over 1, 2, 3, 4, 5, 6, 7, 8, 9, 10, 11, 12, 13, 14, 15, 16, 17, 18, 19, 21, 22, 23 or 24 weeks. In yet further embodiments, the composition is provided over 1, 2, 3, 4, 5, 6, 7, 8, 9, 10, 11, 12, 13, 14, 15, 16, 17, 18, 19, 21, 22, 23 or 24 months. In additional embodiments, the time interval between administrations is 1, 2, 3, 4, 5, 6, 7, 8, 9, 10, 11, 12, 13 or 14 days. In yet other embodiments, the time interval between administrations is 1, 2, 3, 4, 5, 6, 7 or 8 weeks. In additional embodiments, the gel is formulated for cutaneous administration or is administered cutaneously. In still other embodiments, the wound is an ulcer or a burn. In some other aspects, the wound is a diabetic ulcer. In additional embodiments, the wound is a chronic diabetic ulcer. In some embodiments, the wound is a chronic diabetic ulcer of the extremities. In further aspects still, the wound is a chronic diabetic foot ulcer.

In some compositions or methods erythropoietin and/or fibronectin are incorporated into a matrix. In certain aspects, erythropoietin and/or fibronectin are incorporated into the matrix and at least one is cleavable. In other aspects, the matrix incorporates one or more cleavable chemokines, chemoattractants, chemorepellants, growth factors or one or more cleavable cytokines. For example, the chemokine may be one or any combination of chemokines selected from the group consisting of CCL1, CCL2, CCL3, CCL4, CCL5, CCL6, CCL7, CCL8, CCL9/CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2 and CX3CL1. A cytokine for use with the methods or compositions disclosed herein may include members of the IL 17, IL-10, Interleukin, Lymphokine, Monokine, Myokine, Tumor necrosis factor or Proinflammatory cytokine families. Specific examples of cytokines for use with the methods and compositions described herein include one or any combination of GcMAF, Granulocyte colony-stimulating factor, Granulocyte macrophage colony-stimulating factor, Hepatocyte growth factor, IL1A, Interferon, Interferon beta-1a, Interferon beta-1b, Interferon gamma, Interferon type I, Interferon type II, Interferon type III, Interleukin 1 beta, Interleukin 1 receptor antagonist, Interleukin 10, Interleukin 12, Interleukin 15, Interleukin 16, Interleukin 2, Interleukin 23, Interleukin 23 subunit alpha, Interleukin 34, Interleukin 35, Interleukin 6, Interleukin 7, Interleukin 8, Interleukin-1 family, Interleukin-12 subunit beta, Interleukin-36, Leukemia inhibitory factor, Leukocyte-promoting factor, Lymphotoxin, Lymphotoxin alpha, Lymphotoxin beta, Macrophage colony-stimulating factor, Macrophage inflammatory protein, Macrophage-activating factor, Myonectin, Nicotinamide phosphoribosyltransferase, Oncostatin M, Oprelvekin, Platelet factor 4, Promegapoietin, RANKL, Stromal cell-derived factor 1, Tumor necrosis factor alpha or Vascular endothelial growth inhibitor. Growth factors specifically contemplates include, for example, FGF 1, FGF 2, IGF 1, IGF 2, PDGF, EGF, KGF, HGF, VEGF, SDF-1, GM-CSF, CSF, G-CSF, TGF alpha, TGF beta, NGF and ECGF. Also contemplated are hypoxia inducible factors (e.g. HIF-1 alpha and beta and HIF-2), hormones (e.g., insulin, growth hormone (GH). CRH, Leptin, Prolactin and TSH), angiogenic factors (e.g., angiogenin and angiopoietin), coagulation and anticoagulation factors [e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI).

In some embodiments the matrix is a gel. In yet other embodiments the matrix is a hydrogel. In certain instances, a hydrogel refers to three-dimensional hydrophilic cross-linked polymer networks that can absorb large volumes of water and biological fluids without dissolving. Hydrogels may be composed of polymers that are insoluble due to the presence of physical crosslinks (e.g., crystalline regions, intermolecular interactions and entanglements) or chemical crosslinks (e.g., covalent bonding). In specific embodiments, the hydrogel is a fibrin hydrogel or a fibrin domain modified polyethylene glycol hydrogel.

In one embodiment, the hydrogel is a fibrin hydrogel gel which is cross-linked with a cross-linking agent. In certain embodiments, the cross-linked fibrin hydrogel has chemical, physical or mechanical properties that are suitable for their use in implantation into a subject or patient, in particular subcutaneous implantation.

Without limitations, the gel can comprise any ratio of cross-linking agent to fibrin. Accordingly, the gel can comprise a cross-linking agent to fibrin ratio in the range from about 0.1:1 to about 10:1. In some embodiments of the aspects described herein, the gel comprises a cross-linking agent: fibrin ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent: fibrin ratio of 0.20:1 to 0.5:1. In some embodiments, the gel comprises a cross-linking agent: fibrin ratio of 0.25:1 or 0.5:1.

The hydrogels can be made from fibrin solutions comprising a wide concentration range of fibrin. Accordingly, the gel can be made from a fibrin solution comprising from about 50 mg/ml to about 500 mg/ml, from about 100 mg/ml to about 400 mg/ml, 150 mg/ml to about 300 mg/ml, 20 mg/ml to about 250 mg/ml of fibrin, or any range derivable therein. In some embodiments of the aspects described herein, the gel is made from a fibrin solution comprising about 200 mg/ml of fibrin. In some embodiments of the aspects described herein, the hydrogel is made from a fibrin solution comprising about 250 mg/ml of fibrin. In still some other embodiments of the aspects described herein, the hydrogel is made from a fibrin solution comprising about 300 mg/ml of fibrin.

In other embodiments, a hydrogel refers to a polymer that is formed by the free radical polymerization of a hydrophilic monomer solution gelled and crosslinked to form a three-dimensional polymeric meshwork anchoring macromolecules. The macromolecules may comprise a constituent of a ground substance of tissue, such as a native collagen. Collagen may be interspersed within a polymeric meshwork forming a collagen-hydrogel. In some embodiments the collagen hydrogel is capable of promoting epithelial cell growth.

Soluble collagen for cross-linking can be prepared by art-recognized techniques. In addition, other proteins are that support cell attachment and growth may be used to form a cross-linked hydrogel. One example of an additional protein known to support cell growth is fibronectin.

Polysaccharides and mucopolysaccharides can also be added to hydrogels of the present invention.

Hydrogel polymers formed by free radical polymerization of monomer solutions require crosslinking to form the three-dimensional polymeric structure of meshwork to gel the aqueous solution. The addition of crosslinking agents such as ethylene glycol dimethacrylate to the polymerization process can change the resultant hydrogel. Generally, the addition of crosslinking agents tend to increase the rigidity and mechanical strength of the hydrogel. Addition of cross-linking agents, such as ethylene glycol dimethacrylate and methymethacrylate, to the polymerization mixture in the presence of native collagen, still changes the physical properties of the hydrogel, and such additions to the polymerization mixture are compatible with the native collagen, and result in the collagen-hydrogel. Other known crosslinking agents that can be used satisfactorily in producing the collagen-hydrogel include diacrylates and dimethacrylates or other divalent molecules.

Without limitations, the gel can comprise any ratio of cross-linking agent to collagen. Accordingly, the gel can comprise a cross-linking agent to collagen ratio in the range from about 0.1:1 to about 10:1. In some embodiments of the aspects described herein, the gel comprises a cross-linking agent:collagen ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent:collagen ratio of 0.20:1 to 0.5:1. In some embodiments, the gel comprises a cross-linking agent:collagen ratio of 0.25:1 or 0.5:1.

The hydrogels can be made from collagen solutions comprising a wide concentration range of collagen. Accordingly, the gel can be made from a collagen solution comprising from about 50 mg/ml to about 500 mg/ml, from about 100 mg/ml to about 400 mg/ml, 150 mg/ml to about 300 mg/ml, 20 mg/ml to about 250 mg/ml of collagen, or any range derivable therein. In some embodiments of the aspects described herein, the gel is made from a collagen solution comprising about 200 mg/ml of collagen. In some embodiments of the aspects described herein, the hydrogel is made from a collagen solution comprising about 250 mg/ml of collagen. In still some other embodiments of the aspects described herein, the hydrogel is made from a collagen solution comprising about 300 mg/ml of collagen.

Hydrogels, which can be used as synthetic "stimuli-responsive" polymers may be based on synthetic polymers, such as poly (ethylene glycol) (PEG), poly(vinyl alcohol) (PVA), poly(N-isopropylacrylamide) (poly(NiPAAm)). Such hydrogels have been used in numerous regenerative medicine applications (see e.g. N. A. Peppas, P. Bures, W. Leobandung, and H. Ichikawa. Hydrogels in pharmaceutical formulations. Eur. J. Pharm. Biopharm. 50:27-46 (2000)), incorporated herein by reference.

In certain aspects hydrogels are prepared with various polymers such as polyvinyl alcohol (PVA). polyvinyl pyrrolidone (PVP), or polyacrylamides. Exemplary PVA-based hydrogels are disclosed in, e.g., U.S. Pat. Nos: 6,231,605; 5,346,935; 5,981,826; 4,663,358; and 4,988,761, the contents of which are herein incorporated by reference. In certain embodiments polyethylene glycol (PEG) based hydrogels provide a large degree of swelling in aqueous solutions. Various PEG based hydrogels are disclosed in U.S. Patent Nos: 5,514,379; 6,362,276 and 6,541,015, the contents of which are herein incorporated by reference. PCT application WO2006125082, incorporated herein by reference, provides hydrogel formulation containing pre-solidified hydrogel particles in a precursor hydrogel solution.

Without limitations, the gel can comprise any ratio of cross-linking agent to poly (ethylene glycol) (PEG). Accordingly, the gel can comprise a cross-linking agent to PEG ratio in the range from about 0.1:1 to about 10:1. In some embodiments of the aspects described herein, the gel comprises a cross-linking agent:PEG ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent:PEG ratio of 0.20:1 to 0.5:1. In some embodiments, the gel comprises a cross-linking agent: PEG ratio of 0.25:1 or 0.5:1.

The hydrogels can be made from PEG solutions comprising a wide concentration range of PEG. Accordingly, the gel can be made from a PEG solution comprising from about 50 mg/ml to about 500 mg/ml, from about 100 mg/ml to about 400 mg/ml, 150 mg/ml to about 300 mg/ml, 20 mg/ml to about 250 mg/ml of PEG, or any range derivable therein. In some embodiments of the aspects described herein, the gel is made from a PEG solution comprising about 200 mg/ml of PEG. In some embodiments of the aspects described herein, the hydrogel is made from a PEG solution comprising about 250 mg/ml of PEG. In still some other embodiments of the aspects described herein, the hydrogel is made from a PEG solution comprising about 300 mg/ml of PEG.

In another embodiment, the hydrogel is a hyaluronic acid hydrogel gel which is cross-linked with a cross-linking agent. In certain embodiments, the cross-linked hyaluronic acid hydrogel has chemical, physical or mechanical properties that are suitable for their use in implantation into a subject or patient, in particular subcutaneous implantation. In other embodiments, the cross-linked hyaluronic acid hydrogel has chemical, physical or mechanical properties that are suitable for their use in the treatment of dermal wounds of a subject or patient, in particular cutaneous applications.

Without limitations, the gel can comprise any ratio of cross-linking agent to hyaluronic acid. Accordingly, the gel can comprise a cross-linking agent to hyaluronic acid ratio in the range from about 0.1:1 to about 10:1. In some embodiments of the aspects described herein, the gel comprises a cross-linking agent: hyaluronic acid ratio from 0.1:1 to 5:1, from 0.1:1 to 4:1, from 0.1:1 to 2:1, from 0.1:1 to 1.5:1, from 0.1:1 to 1:1, from 0.1:1 to 0.9:1, from 0.2 to 0.8:1, and/or from 0.25 to 0.75:1. In some embodiments, the gel comprises a cross-linking agent: hyaluronic acid ratio of 0.20:1 to 0.5:1. In some embodiments, the gel comprises a cross-linking agent: hyaluronic acid ratio of 0.25:1 or 0.5:1.

The hydrogels can be made from hyaluronic acid solutions comprising a wide concentration range of hyaluronic acid. Accordingly, the gel can be made from a hyaluronic acid solution comprising from about 50 mg/ml to about 500 mg/ml, from about 100 mg/ml to about 400 mg/ml, 150 mg/ml to about 300 mg/ml, 20 mg/ml to about 250 mg/ml of hyaluronic acid, or any range derivable therein. In some embodiments of the aspects described herein, the gel is made from a hyaluronic acid solution comprising about 200 mg/ml of hyaluronic acid. In some embodiments of the aspects described herein, the hydrogel is made from a hyaluronic acid solution comprising about 250 mg/ml of hyaluronic acid. In still some other embodiments of the aspects described herein, the hydrogel is made from a hyaluronic acid solution comprising about 300 mg/ml of hyaluronic acid.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Topical EPO accelerates wound closure and increases blood flow in the regenerating skin of diabetic wounds in a dose-dependent manner; an effect potentiated by FN. Wound closure and blood flow rates in the regenerating skin of non-diabetic and diabetic pigs were determined on day 0, 2, 4, 7, 9, 11 and 14 after the various treatments. (A) Wound closure rates of the vehicle-treated, the FN-treated, the EPO-treated, and the EPO/FN-treated burn wounds in the diabetic pigs. (B) Wound closure rates of the vehicle-treated, the low-dose EPO-treated, and the high-dose EPO-treated burn wounds in the diabetic pigs. (C) Representative photographic images and laser Doppler scans of a vehicle-treated, an FN-treated, an EPO-treated, and an EPO/FN-treated burn wound in a non-diabetic (left) and diabetic pig on day 0, 2, 4, 7, 9, 11 and 14 (right). (D) Representative set of photographic images and laser Doppler scans of the same vehicle-treated, FN-treated, EPO-treated, and EPO/FN-treated burn wounds in a non-diabetic (left) and diabetic pig on day 0, 2, 4, 7, 9, 11 and 14 (right). The white circles in the laser Doppler scans represent the burn wound area on day 0. The dark blue color represents non-vascularized regions, and the yellow and red colors represent vascularized regions with the red-colored regions depicting regions which are more vascularized than the yellow-colored regions. Sample size in each treatment group was 12 except in the low-dose EPO-treated burn wound group where the sample was six. *$p<0.05$ and **$p<0.01$ and is the significance of the difference between the vehicle-treated burn wounds and the other treatments according to the results of a two-way ANOVA with Bonferroni's correction. †$p<0.05$ and is the significance of the difference between (a) the EPO-treated or EPO/FN-treated burn wounds and the FN-treated burn wounds and (b) the high-dose EPO-treated burn wounds and the low-dose EPO-treated burn wounds according to the results of a two-way ANOVA with Bonferroni's correction.

FIG. 2: Topical FN does not affect wound closure and blood flow rates in the regenerating skin of non-diabetic wounds. Wound closure and blood flow rates in the regenerating skin of non-diabetic pigs were determined on day 0, 4, 9 and 14 after the various treatments. (A) Wound closure rates of the vehicle-treated, FN-treated, EPO-treated, and EPO/FN-treated burn wounds in the non-diabetic pigs. (B) Representative set of photographic images (left) and laser Doppler scans (right) of a vehicle-treated, an FN-treated burn wound, an EPO-treated burn wound, and an EPO/FN-treated burn wound in a non-diabetic pig on day 0, 4, 9 and 14. The white circles in the laser Doppler scans represent the burn wound area on day 0. The dark blue color represents non-vascularized regions, and the yellow and red colors represent vascularized regions with the red-colored regions depicting regions which are more vascularized than the yellow-colored regions. Sample size in each treatment group in the two non-diabetic pigs was 12. *$p<0.05$ and **$p<0.01$ and is the significance of the difference between the vehicle-treated burn wounds and the other treatments according to the results of a two-way ANOVA with Bonferroni's correction. †$p<0.05$ and is the significance of the difference between EPO/FN-treated and EPO-treated burn wounds according to the results of a two-tailed Student's t test.

FIG. 3: Topical EPO increases microvascular density (MVD) and eNOS expression in the regenerating skin of diabetic wounds and these effects are potentiated by FN. (A) Representative set of micrographs which show immunohistochemical staining for CD31 expression by vascular endothelial cells of the capillaries in the regenerating skin of the vehicle-, FN-, EPO, and EPO/FN-treated burn wounds of the non-diabetic pigs (upper panel) and of the diabetic pigs (lower panel) that were collected after 14 days of treatment. The MVD in the regenerating skin was determined by counting the number of capillaries in five random microscopic fields (×200 magnification) under a light microscope in each wound site. (B) The MVD in the regenerating skin of the vehicle-treated, the FN-treated, the EPO-treated, and the EPO/FN-treated burn wounds of the non-diabetic pigs. (C) The MVD in the regenerating skin of the vehicle-treated, the FN-treated, the EPO-treated, and the EPO/FN-treated burn wounds of the diabetic pigs. (D and E). Representative western blots of eNOS expression in tissues which were collected on day 14 and then measured in lysates which were prepared from the regenerating skin of vehicle-treated, FN-treated, EPO-treated, and EPO/FN-treated burn wounds of the non-diabetic pigs (D) and diabetic pigs (E). α-Actin was used to normalize protein loading and the blots were derived from samples which were analyzed concomitantly on a separate gel. The sample size of each treatment group was 12 and data are expressed as the average of duplicate measurements ±SD (B and C) for each treatment group. *$p<0.05$ and **$p<0.01$ and is the significance of the difference between the vehicle-treated burn wounds and the other treatments according to the results of a one-way ANOVA with a Tukey's post-hoc test (B and C). †$p<0.05$ and is the significance of the difference between EPO/FN-treated and EPO-treated burn wounds according to the results of a one-way ANOVA with a Tukey's post-hoc test (C). Scale bar: 200 μm (A).

Figure 4A:
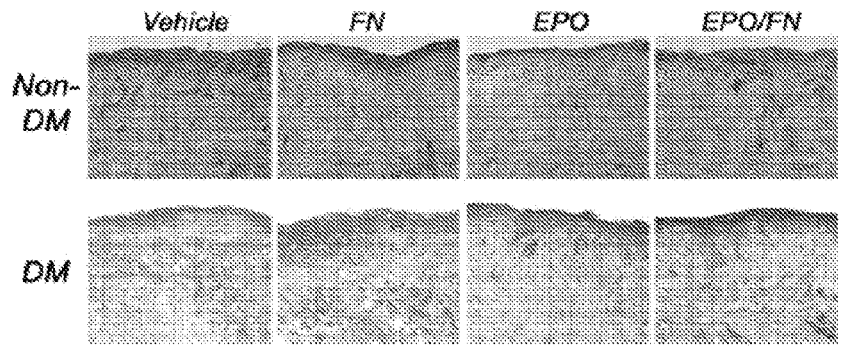
FIG. 4: Topical EPO increases the amount of hydroxyproline (HP) and hyaluronic acid (HA) synthesis in the regenerating skin of diabetic wounds and this effect is potentiated by FN. (A) Representative set of micrographs which show immunohistochemical staining for the amount of HP by Masson's trichrome staining in the regenerating skin of the vehicle-treated, FN-treated, EPO-treated, and EPO/FN-treated burn wounds of the non-diabetic pigs (upper panel) and of the diabetic pigs (lower panel) that were collected after 14 days of treatment. (B) The HP content in regenerating skin of the vehicle-treated, the FN-treated, the EPO-treated, and the EPO/FN-treated burn wounds of the non-diabetic pigs on day 14. (C) The HP amount content in regenerating skin of the vehicle-treated, the FN-treated, the EPO-treated, and the EPO/FN-treated burn wounds of the diabetic pigs. (D) The HA amount in the regenerating skin of the vehicle-treated, the FN-treated, the EPO-treated, and the EPO/FN-treated burn wounds of the non-diabetic pigs. (E) The HA amount in the regenerating skin of the vehicle-treated, the FN-treated, the EPO-treated, and the EPO/FN-treated burn wounds of the diabetic pigs. (F and G). Representative western blots of HAS1 and HAS2 expression levels in tissues which were collected on day 14 and then measured in lysates which were prepared from the regenerating skin of the vehicle-treated, the FN-treated, the EPO-treated, and the EPO/FN-treated burn wounds of the non-diabetic pigs (F) and the diabetic pigs (G). α-Actin was used to normalize protein loading and the blots were derived from samples which were analyzed concomitantly run on a separate gel. The sample size of each treatment group was 12 and the data are expressed as the average of duplicate measurements of HP (B and C) or HA (D and E) amount±SD. *$p<0.05$ and **$p<0.01$ and is the significance of the difference between the vehicle-treated burn wounds and the other treatments according to the results of the one-way ANOVA with Tukey's post-hoc test. †$p<0.05$ and is the significance of the difference between EPO/FN-treated (C) and EPO-treated burn wounds (E) according to the results of a one-way ANOVA with a Tukey's post-hoc test. Scale bars: 200 μm (A).

AQP3 protein expression correlates positively with the extent of angiogenesis and the amounts of hydroxyproline (HP) and hyaluronic acid (HA) in the regenerating skin of diabetic wounds. AQP3 protein expression significantly correlates with (a) the microvascular density (MVD) ($r=0.61$), (b) the amount of HP ($r=0.79$), and (c) the amount of HA ($r=0.88$) in the burn wounds of the non-diabetic pigs. AQP3 protein expression also significantly correlates with (a) the MVD ($r=X$), (b) the HP amount ($r=0.60$) (FIGS. 7C & 7D), and (c) the HA amount ($r=0.93$) (FIGS. 7E & 7F) in the burn wounds of the diabetic pigs ($r=0.88$). Each point represents the average of AQP3 protein expression, the MVD, and the amounts of HP and HA in six wounds.

FIG. 8: AQP3 inhibition by $HgCl_2$ reduces the effect of topical EPO on the wound closure rate, the extent of angiogenesis, and the of hydroxyproline (HP) and hyaluronic acid (HA) amounts in diabetic wounds. The wound closure and blood flow rates in the regenerating skin of diabetic pigs were determined after 14 days of treatment with the vehicle-containing, the high-dose EPO-containing, and the EPO/$HgCl_2$-containing gels. (A) The wound closure rates of the vehicle-treated, the EPO-treated, and the EPO/$HgCl_2$-treated burn wounds of the diabetic pigs. (B) Representative set of photographic images (upper panel) and laser Doppler scans (lower panel) of a vehicle-treated, and EPO-treated, and an EPO/$HgCl_2$-treated burn wound in the diabetic pig after 14 days of treatment. The dark blue color represents non-vascularized regions, and the yellow and red colors represent vascularized regions with red-colored regions representing regions which are more vascularized than the yellow-colored regions. Burn wounds (n=6) in each treatment group in one of the diabetic pigs were assessed and compared. (C) Representative Western blots of eNOS, HAS1, and HAS2 expression levels in tissues which were collected on day 14 and then measured in lysates which were prepared from the regenerating skin of the vehicle-treated, the FN-treated, the EPO-treated, and the EPO/FN-treated burn wounds of the diabetic pigs. α-Actin was used to normalize protein loading and the blots were derived from samples which were concomitantly run on a separate gel (D). The MVD of the regenerating skin of the vehicle-treated, the EPO-treated, and the EPO/$HgCl_2$-treated burn wounds of the diabetic pigs. (E) The HP amount of the regenerating skin of the vehicle-treated, the EPO-treated, and the EPO/HgCl$_2$-treated burn wounds of the diabetic pig. (F) The HA amount of the regenerating skin of the vehicle-treated, the EPO-treated, and the EPO/HgCl$_2$-treated burn wounds of the diabetic pigs. *p<0.05 and p<0.01 and is the significance of the difference between the vehicle-treated burn wounds and the other treatments according to the results a two-way ANOVA with Bonferroni's correction (A). p<0.01 and is the significance of the difference between the vehicle-treated burn wounds and the other treatments according to the results of a one-way ANOVA with Tukey's post-hoc test (D-F). †p<0.05 and is the significance of the difference between the EPO/HgCl$_2$-treated and EPO-treated burn wounds according to the results of a two-tailed Student's t test (D-F).

Figure 9:
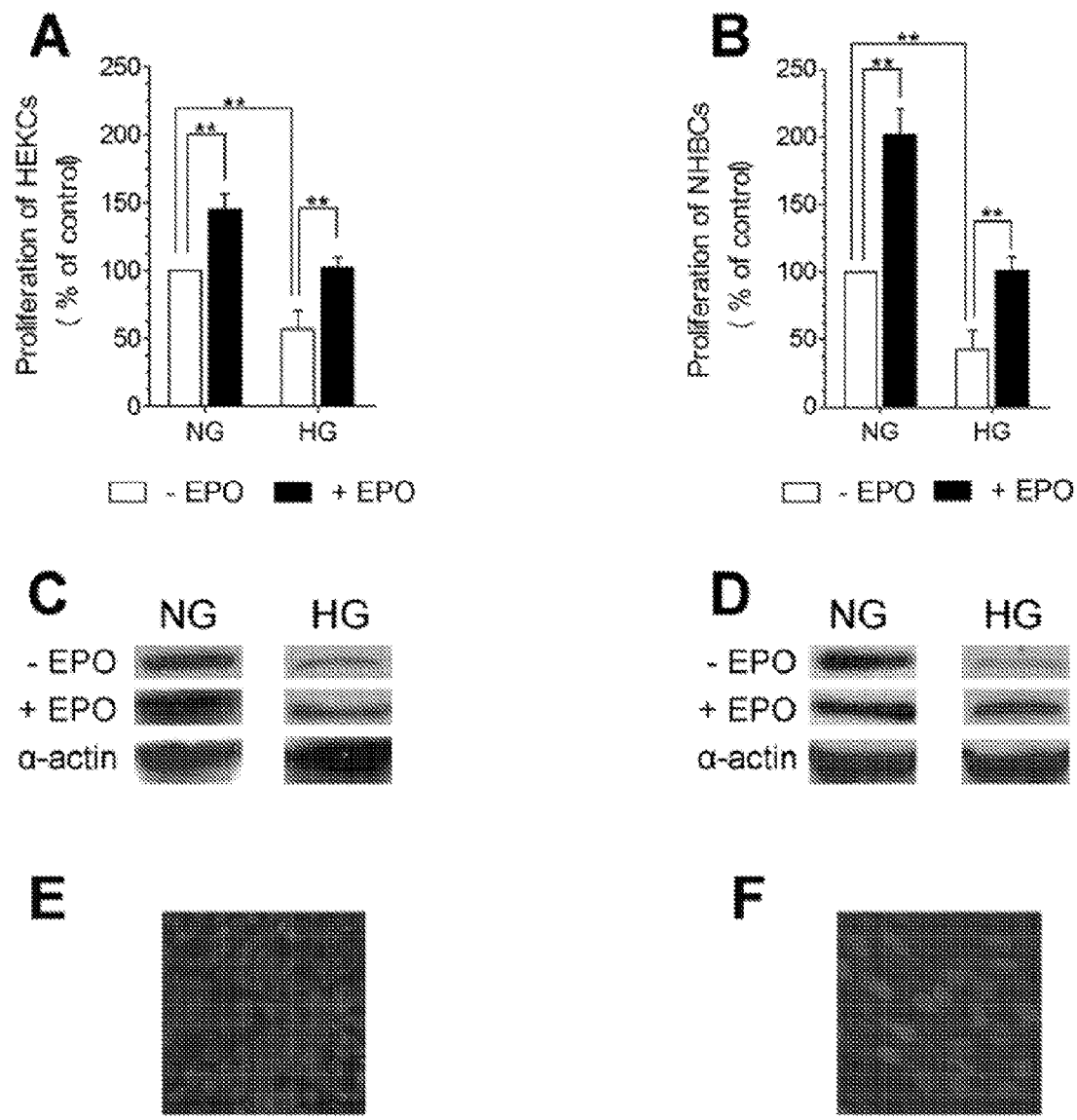

FIG. 9: High glucose downregulates AQP3 expression in keratinocytes and fibroblasts derived from human skin; an effect blocked by EPO. (A) The effect of EPO on the proliferation of HEKCs in a low glucose (normal) and high glucose medium. (B) The effect of EPO on the proliferation of NHBCs in a low glucose (normal, NG) and high glucose (HG) medium (C and D). Representative western blots of AQP3 expression levels in lysates which were prepared EPO-treated HEKCs and NHBCs after a 5-day culture in either a NG or HG medium. α-Actin was used to normalize run on a separate gel (E and F). Representative set of micrographs of immunohistochemical staining for AQP3 expression levels in HEKCs (E) and NHBCs (F). Scale bar: 500 μm. **p<0.01 and is the significance of the difference according to the results of a one-way ANOVA with Tukey's post-hoc test.

Figure 10:
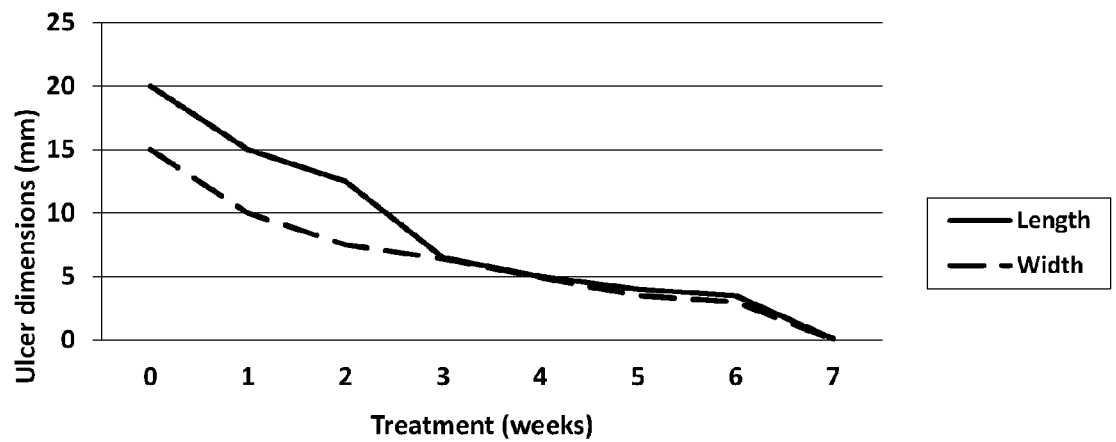

FIG. 10: Line graph showing the decrease in length and width of a chronic diabetic foot ulcer over multiple weeks with EPO/FN treatment.

Figure 11:
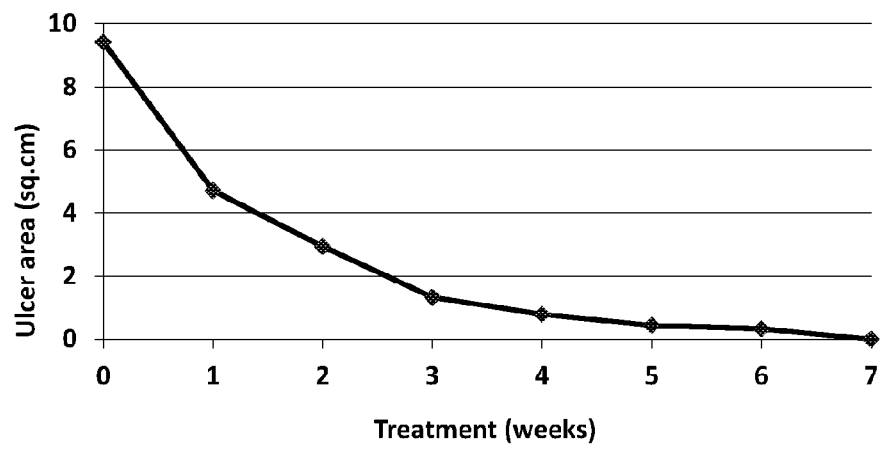

FIG. 11: Line graph showing the decrease in ulcer area of a chronic diabetic foot ulcer over multiple weeks with EPO/FN treatment.

Figure 12:
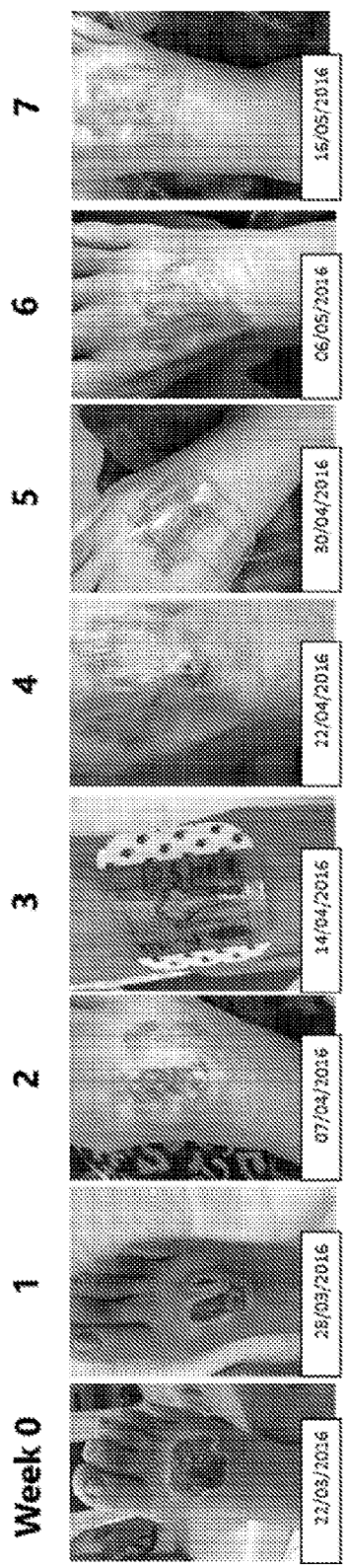

FIG. 12: Representative photos of wound closure of a chronic diabetic foot ulcer over multiple weeks with EPO/FN treatment.

Figure 13:
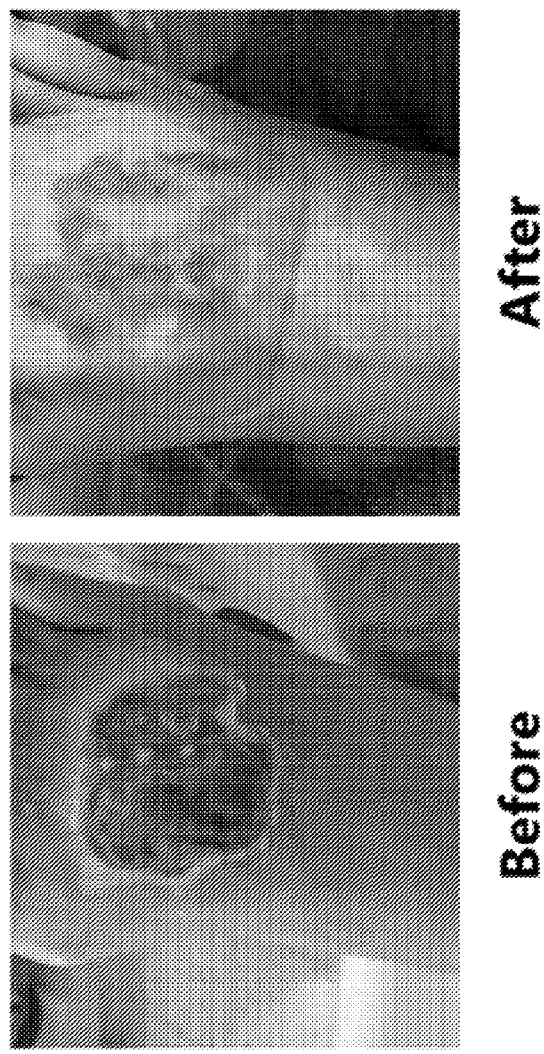

FIG. 13: Representative photos of a chronic diabetic foot ulcer before and after multiple weeks of EPO/FN treatment.

DESCRIPTION OF ILLUSTRATIVE EMBODIMENTS

I. The Present Invention

It is against this background that the present inventor posited that EPO's therapeutically beneficial action on the healing of a DSU is due in part to its ability to stimulate AQP3 expression in skin. This hypothesis was tested in pigs with experimentally-induced type 1 DM and a partial thickness skin burn. It was found that topical EPO treatment of the burns in the diabetic pigs accelerated their healing through an AQP3-dependent mechanism by stimulating angiogenesis and ECM production. Additional evidence suggests that FN can potentiate the accelerating action of EPO on the healing of the burns in diabetic pigs. It is also suggested that diabetic foot wounds can be treated according to the invention. Treatment of humans is also contemplated.

Thus, the present invention relates in part to formulations and treatment of wounds as described above and elsewhere herein. It also relates in in part to a pharmaceutical composition containing a gel, erythropoietin and fibronectin, wherein the fibronectin is present in the composition in an amount potentiates the salutary actions of the erythropoietin when applied to a wound.

A method of treating a wound comprising topically applying a therapeutically effective amount of a formulation such as described above and elsewhere herein to a wound in order to treat and/or accelerate healing the wound, e.g., a burn or a diabetic foot wound.

Without be limited to any particular theory, it is believed that the healing operates via an AQP3-dependent mechanism that activates angiogenesis, triggers collagen and hyaluronic acid synthesis and the formation of the extracellular matrix (ECM), and stimulates reepithelialization by keratinocytes. The addition of fibronectin in the formulation can potentiate the accelerating action of EPO on the healing of the burn injury.

II. Definitions

Thus, according to one aspect of the present invention there is provided a method of promoting wound healing and connective tissue reconstruction in a subject in need thereof. In some embodiments, the subject is diagnosed or suspected of having diabetes. In other embodiments, the subject is diagnosed with or suspected of having high blood sugar or insulin resistance.

The phrase "connective tissue" as used herein refers to animal tissue in which the extracellular matrix (ECM) and specifically collagen, forms the major part, which tissue functions to support and bind other body tissues and parts to one another. A typical example is the skin and internal organs.

The phrase "connective tissue reconstruction" as used herein refers to the restoration of aesthetics, structure, function, and physiology to the damaged or unhealthy tissue. This reconstruction leads to regenerative healing. Furthermore, connective tissue reconstruction refers to the increase in collagen production in the healthy tissue. In an exemplary embodiment, reconstruction leads to a halt in tissue deterioration. in other exemplary embodiments connective tissue reconstruction is devoid of fibrosis.

The phrase "damaged or unhealthy tissue" as used herein refers to a deviation from healthy functional tissue. In the case of skin, a skin that is weaker, less elastic, and is more prone to injury than healthy skin. The structure of unhealthy or damaged skin is inferior to that of healthy skin (for example, the dermis and epidermis contain fewer cells and collagen). One purpose for treating unhealthy skin is to reduce further deterioration of skin and restore its function to normal or near-normal level.

The phrase "healthy tissue" as used herein refers to skin that is strong, elastic, smooth and plump. One purpose of treating healthy skin is to prevent deterioration of skin induced by aging or environmental stress including excessive sunlight and microbial infection.

The term "promoting" in respect to a connective tissue refers to the process of increasing the production of collagen by skin cells such as fibroblasts and keratinocytes, in a manner that allows tissue regeneration. Thus in some embodiments of the present invention, promoting refers to at least about 10%, 20%, 50%, 80% increase in tissue regeneration or at least about 10%, 20%, 50%, 80% arrest in tissue degradation. Those of skill in the art will understand that various methodologies and assays can be used to assess the promotion of tissue regeneration, and similarly, various methodologies and assays may be used to assess the arrest of tissue degradation.

The term "wound" as used herein refers broadly to injuries to the skin and subcutaneous tissue as well as internal organs initiated in any one of a variety of ways (e.g., diabetic ulcers, pressure sores from extended bed rest, wounds induced by trauma, wounds received during or following a surgical procedure and the like) and with varying characteristics. Examples include, but are not limited to, bruises, scrapes, burn wounds, sunburn wounds, incisional wounds, excisional wounds, surgical wounds, necrotizing fascitis, ulcers, venous stasis ulcers, diabetic ulcers, decubitus ulcers, aphthous ulcers, pressure ulcers, scars, alopecia areata, dermatitis, allergic contact dermatitis, atopic dermatitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bulbous pemphigoid, candida, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Pianos Like Keratosis, Lichen Simplex Chronicus, Lichen Sclerosus, Lymphomatoid Papulosis, Lupus of the Skin, Lyme Disease, Lichen Striatus, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, Pityriasis Lichenoides, Pityriasis Rosea, Pityriasis Rubra Pilaris, Plantar Warts, Poison Ivy, Poison Oak, Pompholyx, Pseudofolliculitis Barbae, Pruritus Ani and Pityriasis Alba.

Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III, examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that has not healed within thirty days.

The term "healing" in respect to a wound refers to the process of repairing a wound such as by scar formation (in exemplary embodiments healing is devoid of fibrotic tissue formation).

In a specific embodiment, compositions of some embodiments of the present invention promote i.e., accelerate the healing process.

The phrase "inducing or accelerating a healing process of a skin wound" refers to either the induction of the formation of granulation tissue of wound contraction and/or the induction of epithelialization (i.e., the generation of new cells in the epithelium). Wound healing is conveniently measured by decreasing wound area.

In some aspects the treatment of all wound types, including deep wounds and chronic wounds, is contemplated.

As used herein the term "treating" refers to preventing, curing, reversing, attenuating, alleviating, minimizing, suppressing or halting the deleterious effects of an ischemic condition, such as by enhancing perfusion. Those of skill in the art will understand that various methodologies and assays can be used to assess the development of a condition, and similarly, various methodologies and assays may be used to assess the reduction, remission or regression of the condition.

Treatment can be evaluated by routine experimentation, such as the models described in the Examples section below. Outcome measures such as perfusion and survival, as well as histological and functional criteria, can be employed to assess the efficacy of varying the different parameters, in order to approach optimal efficiency in numbers of cells having maximal therapeutic value in treating skin wounds. Additional parameters known in the art that can be quantified for determining perfusion in an affected tissue are angiography and MRI, and clinical parameters such as extent of tissue necrosis in the affected area, tissue ulceration and amputation of digits and/or limbs.

In the context of wound healing "promoting" refers to the ability to permit or assist wound healing, in a manner that allows treatment thereof. Thus in some embodiments of the present invention, promoting refers to at least about 10%, 20%, 50%, 80% reduction in time taken to achieve healing or at least about 10%, 20%, 50%, 80% increase in wound closure.

As used herein the term "subject" refers to any mammal, (e.g., a human being or domesticated animals), male or female at any age that experiences or may experience tissue damage or suffers from a wound or from ischemia, at any stage and/or degree.

As mentioned, the method according to this aspect of the present invention is achieved by topically administering to the subject the indicated dosages of EPO and FN.

As used herein the term "erythropoietin" (EPO) refers to a mammalian (e.g., human) erythropoietin protein (interchangeably used with polypeptide) or mimetics thereof such as set forth in GenBank Accession No. NP_000790. Erythropoietin may be synthesized using recombinant DNA techniques or solid phase technology. Erythropoietin is also commercially available (e.g., Cytolab/Peprotech, Rehovot, Israel; Arenesp, Amgen, Thousand Oaks, Calif., USA; and Epogen, Amgen, Thousand Oaks. Calif., USA, Bristol-Myers Squibb, Roche and Sanofi-Aventis). Erythropoietin may be used as an entire glycoprotein or as only a protein subunit devoid of the bound sugar. Since the erythropoietin of the present embodiments is used for clinical applications, it is preferably sterile or may be purified of possible contaminating factors (e.g., bacteria or bacterial components, such as by filter).

As used herein the term "fibronectin" (FN) refers to a mammalian (e.g., human) fibronectin protein (interchangeably used with polypeptide) or mimetics thereof such as set forth in GenBank Accession No. NP_002017. Fibronectin may be synthesized using recombinant DNA techniques or solid phase technology. Fibronectin is also commercially available (e.g., Chemicon international Inc., Temecula, Calif., USA). Since the fibronectin of the present invention is used for clinical applications, it is preferably sterile or may be purified of possible contaminating factors (e.g., bacteria or bacterial components, such as by filter).

It will be appreciated that when mimetics compositions are used the dosages of FN and EPO should be calibrated such as according to the molar value. Such a calibration is a routine calculation for those of ordinary skill in the art.

Pharmaceutical or cosmetic compositions of the present invention may comprise erythropoietin and fibronectin in a co-formulation (such as provided in Example 1 further below) or in two separate compositions.

As used herein the phrase "topically administering" refers to applying or spreading the compositions of the present invention onto the surface of the body, i.e. skin, scalp, hair, nails and the like, preferably on the surface of the damaged tissue (e.g., skin), wound or on the surface of a wound or a diabetic ulcer. When not co-formulated, administration of erythropoietin and fibronectin may be effected concomitantly or sequentially.

It will be appreciated that the dose of erythropoietin and fibronectin applied according to the teachings of the present invention may vary. Thus, erythropoietin can be administered at a dose between 10-30 μg per $cm^2$ tissue depending on the severity of the tissue damage or wound to be treated. In one embodiment the dose of erythropoietin is between 15-25 μg per $cm^2$ tissue. In another embodiment the dose of erythropoietin is about 20 μg per $cm^2$ tissue. Fibronectin can be administered at a dose between 100-300 μg per $cm^2$ tissue depending on the severity of the tissue damage or wound to be treated. In one embodiment the dose of fibronectin is between 150-250 μg per $cm^2$ tissue. In another embodiment the dose of fibronectin is about 200 μg per $cm^2$ tissue.

In particular embodiments the dose of erythropoietin administered is between 0.1-10 μg per $cm^2$ tissue. In other embodiments the dose of fibronectin administered is between 10-100 μg per $cm^2$ tissue. In certain embodiments the dose of erythropoietin and/or fibronectin is adapted for use in cosmetics. For example, the dose of erythropoietin and/or fibronectin may be adapted to treat scratched skin. Thus, the formulations of the invention may also be used cosmetically and/or for small wound healing to treat as for skin conditions with small or minor wounds as a result of scratches, soft skin fissures, acne, and the like to name a few non-limiting examples. Thus, the present invention relates in part to a method of cosmetically treating a scratched skin surface by applying a sufficient amount of the compositions of the invention to a scratched skin surface to cosmetically treat the surface, for example, where the scratched skin surface is the result of a scratch, a soft skin fissure, acne and the like.

The present invention also relates to a method of healing a scratched skin surface by applying a sufficient amount of the compositions of the present invention to a scratched skin surface to heal the scratched skin surface, for example, where the scratched skin surface is the result of a scratch, a soft skin fissure, acne and the like.

The compositions including erythropoietin and/or fibronectin of the embodiments can be administered to the subject per se or in a pharmaceutical or cosmetic composition. In some aspects erythropoietin and/or fibronectin of the embodiments are formulated in a matrix. In specific aspects the matrix is a gel. In other specific embodiments the gel is a hydrogel.

As used herein a "pharmaceutical or cosmetic composition" refers to a preparation of the active ingredients described herein with other chemical components such as physiologically suitable carriers and excipients. The purpose of the composition is to facilitate administration of the active ingredients (e.g., EPO and FN) to the subject.

As used herein the term "active ingredient" refers to the erythropoietin and fibronectin compositions accountable for the intended biological effect (i.e., promoting wound healing, connective tissue reconstruction and treating ischemia).

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the composition (pharmaceutical composition or cosmetic composition) to further facilitate administration of an active ingredient of the present invention.

Techniques for formulation and administration of drugs may be found in "Remington's Pharmaceutical Sciences," Mack Publishing Co Easton, Pa., latest edition, which is incorporated herein by reference.

The composition may be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an adhesive bandage, a non-adhesive bandage, a wipe, a baby wipe, a gauze, a pad and a sanitary pad.

The unit dosage form according to the teachings of the present invention may comprise erythropoietin at a dose of about 10-30 μg, fibronectin at a dose of about 100-300 μg, or both erythropoietin at a dose of about 10-30 μg and fibronectin at a dose of about 100-300 μg. In one embodiment, the unit dosage form comprise erythropoietin at a dose of about 15-25 μg, fibronectin at a dose of about 150-250 μg, or both erythropoietin at a dose of about 15-25 μg and fibronectin at a dose of about 150-250 μg. In another embodiment, the unit dosage form comprise erythropoietin at a dose of about 20 μg, fibronectin at a dose of about 200 μg, or both erythropoietin at a dose of about 20 μg and fibronectin at a dose of about 200 μg. Additionally, the unit dosage form according to the teachings of the present invention may comprise erythropoietin at a dose of about 0.1-10 μg, fibronectin at a dose of about 10-100 μg, or both erythropoietin at a dose of about 0.1-10 μg and fibronectin at a dose of about 10-100 μg.

The quantity of active compound in a unit dose of preparation may be varied or adjusted according to the particular application.

The compositions (e.g., pharmaceutical or cosmetic compositions) of the present invention may be applied in a local manner, for example, via administration of the compositions directly onto a tissue region (e.g. wound) of a patient. Suitable routes of administration of the compositions may, for example, include topical (e.g., to a keratinous tissue, such as the skin, hair, nail, scalp) and mucosal (e.g., oral, vaginal, eye) administrations.

The compositions of the present invention may also be applied via injecting the composition including the active ingredient (e.g., EPO and FN) and a physiologically acceptable carrier. For local administration, the compositions may be injected into the wound, and/or into healthy skin that surrounds the wounded skin, or both.

Compositions of the present invention may be manufactured by processes well known in the art, e.g., by means of conventional mixing, dissolving, granulating, dragee-making, levigating, emulsifying, encapsulating, entrapping or lyophilizing processes.

The active ingredient may also be in a powder form for constitution with a suitable vehicle, e.g., sterile, pyrogen-free water based solution, before use.

Compositions for use in accordance with the present invention thus may be formulated in conventional manner using one or more physiologically acceptable carriers comprising excipients and auxiliaries, which facilitate processing of the active ingredients into preparations. Proper formulation is dependent upon the administration. approach chosen.

Determination of a therapeutically effective amount is well within the capability of those skilled in the art, especially in light of the detailed disclosure provided herein.

For any preparation used in the method of the invention, the (therapeutically) effective amount or dose can be estimated initially from in vitro assays. In addition, a dose can be formulated in tissue cultures systems or in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exacrt formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition (e.g., the area, depth and degree of the tissue damage, wound or the ischemia) and the responsiveness of the tissue, dosing can be of a single or a plurality of administrations, with course of treatment lasting from several days to several weeks or until cure is effected or diminution of the skin condition is achieved. Preferably, the compositions of the present invention are administered at least once a day.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA-approved kit, which may contain one or more-unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

Since the compositions of the present invention are utilized in vivo, the compositions are preferably of high purity and substantially free of potentially harmful contaminants, e.g., at least National Food (NF) grade, generally at least analytical guide, and preferably at least pharmaceutical grade. To the extent that a given compound must be synthesized prior to use, such synthesis or subsequent purification shall preferably result in a product that is substantially free of any potentially contaminating toxic agents that may have been used during the synthesis or purification procedures.

Additional factors may be incorporated into the compositions or gels of the present invention (i.e., erythropoietin and fibronectin described hereinabove). These include, but are not limited to, extracellular matrix components (e.g. vitronectin, laminin, collagen, elastin), growth factors (e.g. FGF 1, FGF 2, IGF 1, IGF 2, PDGF, EGF, KGF, HGF, VEGF, SDF-1, GM-CSF, CSF, G-CSF, TGF alpha, TGF beta, NGF and ECGF), hypoxia inducible factors (e.g. HIF-1 alpha and beta and HIF-2), hormones (e.g., insulin, growth hormone (GH), CRH, Leptin, Prolactin and TSH), angiogenic factors (e.g., angiogenin and angiopoietin), coagulation and anticoagulation factors [e.g., Factor I, Factor XIII, tissue factor, calcium, vWF, protein C, protein S, protein Z, fibronectin, antithrombin, heparin, plasminogen, low molecular weight heparin (Clixan), high molecular weight kininogen (HMWK), prekallikrein, plasminogen activator inhibitor-1 (PAI1), plasminogen activator inhibitor-2 (PAI2), urokinase, thrombomoduline, tissue plasminogen activator (tPA), alpha 2-antiplasmin and Protein Z-related protease inhibitor (ZPI)], cytokines (IL-1 alpha, IL-1 beta, IL-2, IL-3, IL-4, IL-5, IL-6, IL-7, IL-8, IL-9, IL-10, IL-11, IL-12, IL-13 and INF-alpha, INF, beta, and INF-gamma), chemokines (e.g., MCP-1 or CCL2), enzymes (e.g. endoglycosidases, exoglycosidases, endonucleases, exonucleases, peptidases, lipases, oxidases, decarboxylases, hydrases, chondroitinase, chondroitinase ABC, chondroitinase AC, hyaluronidase, keratanase, heparanases, heparanase splice variance, collagenase, trypsin, catalases), neurotransmitters (e.g., acetylcholine and monoamines), neuropeptides (e.g. substance P), vitamins (e.g., D-biotin, Choline, Chloride, Folic acid, Myo-inositol, Niacinamide, D-Pantothenic acid, Calcium salts, Pyridoxal.HCl, Pyrodixine.HCl, Riboflavin, Thiamine.HCl, Vitamin B 12, vitamin E, vitamin C, vitamin D, vitamin B 1-6, vitamin K, vitamin A and vitamin PP), carbohydrates (e.g. Mono/Di/Polysacharides including glucose, mannose, maltose and fructose), ions, chelators (e.g. Fe chelators, Ca chelators), antioxidants (e.g., Vitamin E, Quarcetin, superoxide scavengers, Superoxide dismutase), H2O2 scavengers, free radicals scavengers, Fe scavengers), fatty acids (e.g., Triglycerides, Phospholipids, Cholesterols, free fatty acids and non free fatty acids, fatty alcohol, Linoleic acid, oleic acid and lipoic acid), antibiotics (e.g., Penicillins, Cephalosporins and Tetracyclines), analgesics, anesthetics, antibacterial agents, anti-yeast agents, anti-fungal agents, antiviral agents, pro-biotic agents, anti-protozal agents, anti-pruritic agents, anti-dermatitis agents, anti-emetics, anti-inflammatory agents, anti-hyperkeratolyic agents, antiperspirants, anti-psoriatic agents, anti-seborrheic agents, antihistamine agents, amino acids (e.g., essential and non essential (from A-Z) especially glutamine and arginine), salts (e.g., prurivat salts and sulfate salts), sulfates (e.g. Calcium Sulfate), steroids (e.g., androgens, estrogens, progestagens, glucocorticoids and mineralocorticoids), catecholamines (e.g., Epinephrine and Norepinephrine), Nucleosides and Nucleotides (e.g., Purins and Pyrimidines), Prostaglandins (e.g. Prostaglandin E2), Leucotriens, Erythropoietins (e.g. Thrombopoietin), Proteoglycans (e.g. Heparan sulfate, keratan sulfate), Hydroxyapatites [e.g. Hydroxyapatite $(Ca_{10}(PO_4)_6(OH)_2)$], Haptoglobins (Hp1-1, Hp2-2 and Hp1-2), Superoxide dismutases (e.g. SOD 1/2/3), Nitric Oxides, Nitric Oxide donors (e.g. nitroprusside, Sigma Aldrich, St. Louis, Mo., USA, Glutathione peroxidases, Hydrating compounds (e.g. vasopressin), cells (e.g. Platelets), cell medium (e.g. M199, DMEM/F12, RPMI, Iscovs), serum (e.g. human serum, fetal calf serum, fetal bovine serum), buffers (e.g., HEPES, Sodium Bicarbonate), detergents (e.g., Tween), disinfectants, herbs, fruit extracts, vegetable extracts (e.g. cabbage, cucumber), flower extracts, plant extracts, flavinoids (e.g. pomegranate juice), spices, leafs (e.g. Green tea, Chamomile), Polyphenols (e.g. Red Wine), honey, lectins, microparticies, nanoparticles (lyposomes), micelles, calcium carbonate (CaCO3, e.g. precipitated calcium carbonate, ground/pulverized calcium carbonate, albacar, PCC, GCC), calcite, limestone, crushed marble, ground limestone, lime, chalk (e.g. whiting chalk, champagne chalk, french chalk) and co factors such as BH4 (tetrahydrobiobterine).

The present composition ma also contain ingredients, substances, elements and materials containing, hydrogen, alkyl groups, aryl groups, halo groups, hydroxy groups, alkoxy groups, alkylamino groups, dialkylamino groups, acyl groups, carboxyl groups, carboamido groups, sulfonamide groups, aminoacyl groups, amide groups, amine groups, nitro groups, organo selenium compounds, hydrocarbons, and cyclic hydrocarbons.

The present composition may be combined with substances such as benzol peroxide, vasoconstrictors, vasodilatators, salicylic acid, retinoic acid, azelaic acid, lactic acid, glycolic acid, pyreuric acid, tannins, benzlidenecamphor and derivatives thereof, alpha hydroxyis, surfactants.

Compositions of some embodiments of the present invention may be bioconjugated to polyethylenglycol (e.g. PEG, SE-PEG) which preserves the stability (e.g., against protease activities) and/or solubility (e.g., within a biological fluid such as blood, digestive fluid) of the active ingredients (i.e. EPO and/or FN compositions of the present invention) while preserving their biological activity and prolonging its half-life.

In addition to the pharmaceutically effective amount of an agent disclosed herein, the compositions of this aspect of the present invention also include a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals.

In order to enhance the percutaneous absorption of the active ingredients (e.g., erythropoietin and/or fibronectin of the present invention), one or more of a number of agents can be added to the compositions including, but not limited to, dimethylsulfoxide, dimethylacetamide, dimethylformamide, surfactants, axone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion, a soap, a paste, an emulsion, a gel, a spray or an aerosol. As will be understood by the skilled artisan, a given component will distribute primarily into either the water or oil/silicone phase, depending on the water solubility/dispersibility of the component in the composition.

Emulsions according to the present invention generally contain a pharmaceutically effective amount of an agent disclosed herein and a lipid or oil. Lipids and oils may be derived from animals, plants, or petroleum and may be natural or synthetic (i.e., man-made). Examples of suitable emulsifiers are described in, for example, U.S. Pat. No. 3,755,560, issued to Dickert, et al., Aug. 28, 1973; U.S. Pat. No. 4,421,769, issued to Dixon, et al., Dec. 20, 1983 and McCutcheon's Detergents and Emulsifiers, North American Edition, pages 317-324 (1986), each of which is fully incorporated by reference in its entirety.

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form.

Examples of suitable carriers comprising oil-in-water emulsions are described in U.S. Pat No. 5,073,371 to Turner, D. J. et al., issued Dec. 17, 1991, and U.S. Pat No. 5,073,372, to Turner, D. J. et al., issued Dec. 17, 1991 each of which is fully incorporated by reference in its entirety. An especially preferred oil-in-water emulsion, containing a structuring agent, hydrophilic surfactant and water, is described in detail hereinafter.

A preferred oil-in-water emulsion comprises a structuring agent to assist in the formation of a liquid crystalline gel network structure. Without being limited by theory, it is believed that the structuring agent assists in providing theological characteristics to the composition which contribute to the stability of the composition. The structuring agent may also function as an emulsifier or surfactant.

A wide variety of anionic surfactants are also useful herein. See, e.g., U.S. Pat. No. 3,929,673, to Laughlin et al., issued Dec. 30, 1975 which is fully incorporated by reference in its entirety. In addition, amphoteric and zwitterionic surfactants are also useful herein.

The compositions of the present invention can be formulated in any of a variety of forms utilized by the pharmaceutical industry for skin application including solutions, lotions, sprays, creams, ointments, salves, gels, oils, wash, etc., as described below.

The compositions of the present invention may be formulated viscous enough to remain on the treated skin area, does not readily evaporate, and/or is not easily removed by rinsing with water, but rather is removable with the aid of soaps, cleansers and/or shampoos.

Methods for preparing compositions having such properties are well known to those skilled in the art, and are described in detail in Remington's Pharmaceutical Sciences, 1990 (supra); and Pharmaceutical Dosage Forms and Drug Delivery Systems, 6th ed., Williams & Wilkins (1995).

The topical compositions of the subject invention, including hut not limited to lotions and creams, may comprise a dermatologically acceptable emollient. As used herein, "emollient" refers to a material useful for the prevention or relief of dryness, as well as for the protection of the skin. Wide varieties of suitable emollients are known and may be used herein. See, e.g., Sagarin, Cosmetics, Science and Technology, 2nd Edition, Vol. 1, pp. 3243 (1972), which contains numerous examples of materials suitable as an emollient and is fully incorporated herein by reference. A preferred emollient is glycerin.

Lotions and creams according to the present invention generally comprise a solution carrier system and one or more emollients.

The topically applied composition of the present invention may also include additional components which are added, for example, in order to enrich the compositions with fragrance and skin nutrition factors.

Such components are selected suitable for use on human keratinous tissue without inducing toxicity, incompatibility, instability, allergic response, and the like within the scope of sound medical judgment. In addition, such optional components are useful provided that they do not unacceptably alter the benefits of the active compounds of the invention.

The CTFA Cosmetic Ingredient Handbook, Second Edition (1992) describes a wide variety of non-limiting cosmetic ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyffhizinate), skin treating agents, thickeners, and vitamins and derivatives thereof.

The compositions of the present invention can be applied directly to the skin. Alternatively, it can be delivered via normal skin application by various transdermal drug delivery systems which are known in the art, such as transdermal patches that release the composition into the skin in a time released manner. Other drug delivery systems known in the arts include pressurized aerosol bottle, iontophoresis or sonopharesis. Iontophoresis is employed to increase skin permeability and facilitate transdermal delivery. U.S. Pat. Nos. 5,667,487 and 5,658,247 discloses an ionosonic apparatus suitable for the ultrasonic-iontophoretically mediated transport of therapeutic agents across the skin. Alternatively, or in addition, liposomes or micelles may also be employed as a delivery vehicle.

Since wounds and ischemia may engage the scalp, the compositions of the present invention further include emollients, surfactants and/or conditioners which are suitable for use on the scalp skin and hair.

The emollients include, but are not limited to, hydrocarbon oils and waxes, such as mineral oil, petrolatum, and the like, vegetable and animal oils and fats, such as olive oil, palm oil, castor oil, corn oil, soybean oil, and the like, and lanolin and its derivatives, such as lanolin, lanolin oil, lanolin wax, lanolin alcohols, and the like. Other emollients include esters of fatty acids having 10 to 20 carbon atoms, such as including myristic, stearic, isostearic, palmitic, and the like, such as methyl myristate, propyl myristate, butyl myristate, propyl stearate, propyl isostearate, propyl palmitate, and the like. Other emollients include fatty acids having 10 to 20 carbon atoms, including stearic, myristic, isostearic, and the like. Emollients also include fatty alcohols having ten to twenty carbon atoms, such as cetyl, myristyl, isostearyl, stearyl and the like.

An emulsifier/surfactant is preferably utilized when formulating the compositions of the present invention for use on hair.

Examples of surfactants include, hut are not limited to, spolyoxyalkylene oxide condensation products of hydrophobic alkyl, alkene, or alkyl aromatic functional groups having a free reactive hydrogen available for condensation with hydrophilic, alkylene oxide, polyethylene oxide, propylene oxide, butylene oxide, polyethylene oxide or polyethylene glycol. Particularly effective are the condensation products of octylphenol with about 7 to about 13 moles of ethylene oxide. sold by the Rohm & Haas Company under their trademark TRITON 100® series products.

Other ingredients such as, fragrances, stabilizing agents, dyes, antimicrobial agents, antibacterial agents, anti agglomerates, ultraviolet radiation absorbers, and the like are also included in the composition of the embodiments.

A conditioner agent stable to acid hydrolysis, such as a silicone compound having at least one quaternary ammonium moiety along with an ethoxylated monoquat is preferably also utilized in order to stabilize and optionally thicken the composition of the embodiments.

Materials that can be used to opacify compositions of the invention include fatty esters, opacifying polymers, such as styrene polymers, like OPACIFIER 653™ from Morton, International, Inc.; and fatty alcohols. The following is a non-limiting list of fatty alcohols: cetyl alcohol; stearyl alcohol; cetearyl alcohol; behenyl alcohol; and arachidyl alcohol. Conditioning compositions of the invention which are not clear also can include Lexamine S-13, dicetylammonium chloride, and ceteareth-20.

In a specific embodiment, the erythropoietin and fibronectin formulation comprises about 10-30 μg/mL, erythropoietin and about 100-300 μg/mL Fibronectin, about 0.20% Methyl Paraben, about 9% Laureth and Isoparafin and Polyacrylamide, about 12% Deionized Water, and up to 100% Phosphate Buffer Solution.

In yet another embodiment, the erythropoietin and fibronectin formulation comprises erythropoietin (EPO) (5% w/w), fibronectin (FN) (30% w/w), glycerol (5%, w/w), carbomer 940 (1%, w/w), benzyl alcohol (BA) (2%, w/w), triethanolamine (0.9%, w/w) methylparaben (0.2%, w/w), propylparaben (PP) (0.05%, w/w) and water (to 100%, w/w).

In still other embodiments, an erythropoietin and fibronectin formulation or composition comprises erythropoietin at a concentration of any value between 0.01% to 30% (w/w), fibronectin at a concentration of any value between 0.01% to 50% (w/w), glycerol at a concentration of any value between 0.01% to 30% (w/w), Carbomer 940 at a concentration of any value between 0.01% to 30% (w/w), benzyl alcohol at a concentration of any value between 0.01% to 30% (w/w), triethanolamine at a concentration of any value between 0.01% to 30% (w/w), methylparaben at a concentration of any value between 0.01% to 30% (w/w), propylparaben at a concentration of any value between 0.01% to 30% (w/w) and water at a concentration of any value between 0.01% to 100% (w/w).

Thus embodiments of the present invention comprise topical compositions for promoting angiogenesis and wound healing.

It will be appreciated that compositions of the present invention can be used in combination with other currently practiced therapies such as, without being limited to, photo/light therapy (e.g., Dermanwand™ for Wound Care by National Biological Corp. Beachwood, Ohio) and ultrasound therapy (see e.g., U.S. Pat. No. 6,960,173).

It is expected that during the life of a patent maturing from this application many relevant erythropoietin and fibronectin compositions will be developed and the scope of the term erythropoietin and fibronectin compositions is intended to include all such new technologies a priori.

As used herein the term "about" refers to ±10%.

Erythropoietin and fibronectin compositions and formulations are described in US2014/0154205 A1 ("Erythropoietin And Fibronectin Compositions For Therapeutic And Cosmetic Applications") and in US2010/0310626 A1 ("Erythropoietin And Fibronectin Compositions For Bone Regeneration"), the contents of both of which are incorporated by reference herein in their entirety.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Four pigs, two pigs with DM and two control pigs, completed the 14-day study period. The two diabetic pigs had significantly higher blood glucose and glycosylated hemoglobin (HbA1c) levels and lower body weights than the two control pigs. Topical treatment of the burns with the vehicle-, FN-, EPO- and EPO/FN-containing gels did not change (a) the red blood cell, leukocyte, or platelet counts and the elevated blood glucose levels in the diabetic pigs, and (b) the blood hemoglobin and HbA1c levels in the control and diabetic pigs (Table 1).

TABLE 1

Effect of diabetes mellitus on pig's body weight and topical wound treatment on hematology.

|  | Non-diabetic Pigs (n = 2) | | | Diabetic Pigs (n = 2) | | |
| --- | --- | --- | --- | --- | --- | --- |
|  | Day 0 | Day 7 | Day 14 | Day 0 | Day 7 | Day 14 |
| Body weight (kg) | 68 ± 3 | 73 ± 4 | 78 ± 4 | 54 ± 3* | 53 ± 3* | 52 ± 3* |
| Blood glucose levels (mg/dl) | 109 ± 8 | 99 ± 10 | 102 ± 7 | 587 ± 123* | 601 ± 134* | 569 ± 187* |
| HbA1c (%) | 5.1 ± 0.3 | 4.9 ± 0.3 | 5.0 ± 0.3 | 5.3 ± 0.4 | 5.2 ± 0.4 | 5.5 ± 0.4 |
| RBC count ($10^6/\mu l$) | 7.2 ± 0.4 | 6.9 ± 0.3 | 7.4 ± 0.5 | 6.8 ± 0.4 | 6.6 ± 0.5 | 7.0 ± 0.7 |
| Leukocyte count ($10^3/\mu l$) | 17.6 ± 0.7 | 18.2 ± 0.9 | 18.0 ± 0.8 | 19.6 ± 1.1 | 17.5 ± 0.8 | 18.3 ± 0.9 |
| Platelet count ($10^3/\mu l$) | 407 ± 71 | 461 ± 92 | 387 ± 69 | 419 ± 73 | 428 ± 82 | 456 ± 101 |
| Hemoglobin levels | 9.6 ± 0.6 | 10.7 ± 0.9 | 10.7 ± 1.1 | 8.8 ± 0.7 | 10.9 ± 1.2 | 10.8 ± 0.9 |

Values are presented as mean ± standard deviation. (n) number of pigs. Statistical significance is set at 5%.
*$p < 0.05$ and is the significance of the difference within the group between day 0, 7 and day 14, NS; not significant; RBC, red blood cells; HbA1c, glycated hemoglobin.

Topical EPO accelerates wound closure and increases blood flow in the regenerating skin of diabetic wounds in a dose-dependent manner and this effect is potentiated by FN. The EPO-treated, the FN-treated, and the EPO/FN-treated diabetic wounds closed faster than the vehicle-treated diabetic wounds. The most significant differences in wound closure rates were detected between the vehicle-treated and the EPO/FN-treated diabetic wounds from day 4 onward. From day 4 onward, the wound closure rate of the EPO/FN-treated wounds was significantly faster than that of the FN-treated and the EPO-treated diabetic wounds. From day 9 onward, the wound closure rate of the EPO-treated diabetic wounds was faster than that of FN-treated diabetic wounds (FIG. 1A).

The wound closure rate of the vehicle-treated diabetic wounds was significantly slower than that of the vehicle-treated healthy wounds. The wound closure rates of the EPO-treated diabetic wounds were dose-dependent. The wound closure rates of the high-dose EPO-treated diabetic wounds were significantly faster than those of the low-dose EPO-treated diabetic wounds. Additionally, the wound closure rates of the low-dose EPO-treated diabetic wounds were significantly faster than those of the vehicle-treated diabetic wounds (FIG. 1B).

Blood flow in the vehicle-treated diabetic wounds was less than that in the vehicle-treated non-diabetic wounds from day 2 onwards. IT was also discovered that the blood flow in the EPO-treated diabetic wound was not significantly different from that of the EPO/FN-treated diabetic wounds, and these two blood flows were significantly higher than those in the vehicle-treated and FN-treated diabetic wounds (FIG. 1C; right panel). The blood flow in the high-dose EPO-treated diabetic wounds was significantly higher than that in the vehicle-treated diabetic wounds from day 4 onwards and that in the low-dose EPO-treated diabetic wounds from day 7 onwards. The blood flow in the low-dose EPO-treated diabetic wounds was significantly higher than that in the vehicle-treated diabetic wounds from day 9 onwards (FIG. 1D; right panel).

Topical FN does not affect wound closure and blood flow in the regenerating skin of non-diabetic wounds. The wound closure rates and blood flow of the vehicle-treated and FN-treated wounds of healthy pigs were very similar. From day 4 onward, the wound closure rates and blood flow of the EPO-treated non-diabetic wounds were significantly greater than those of the vehicle-treated and FN-treated non-diabetic wounds. Interestingly, the most significant differences in wound closure rates and blood flow were detected between the EPO/FN-treated wounds and the vehicle-treated, the FN-treated, and the-EPO-treated wounds in the healthy pigs over the period from day 4 to day 11 (FIG. 2A & 2B).

Topical EPO increases the microvascular density (MVD) and eNOS expression levels in the regenerating skin of diabetic wounds and FN potentiates these effects. The MVD and eNOS expression levels in the vehicle-treated diabetic wounds were lower than those in the vehicle-treated non-diabetic wounds after 14 days (FIGS. 3A-E). Topical FN treatment for 14 days had no effect on the MVD and eNOS expression levels in the diabetic and non-diabetic wounds (FIGS. 3B-E). On the other hand, topical EPO treatment for 14 days significantly increases the MVD and eNOS expression levels in the diabetic and non-diabetic wounds (FIGS.

3B-E). In the EPO/FN-treated non-diabetic wounds, the MVD and eNOS expression levels were not significantly different from those in the EPO-treated non-diabetic wounds (FIGS. 3B & 3D). In contrast, the MVD and eNOS expression levels of the EPO/FN-treated diabetic wounds were significantly higher than those in the EPO-treated diabetic wounds (FIGS. 3C & 3E).

Figure 4B:
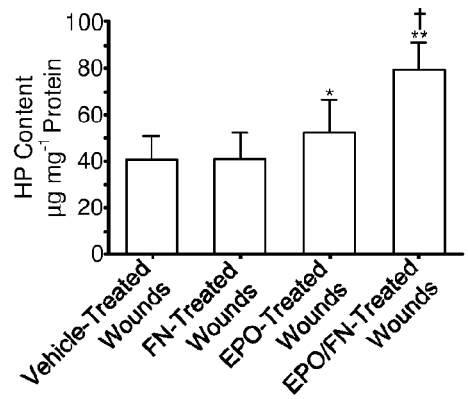
Figure 4C:
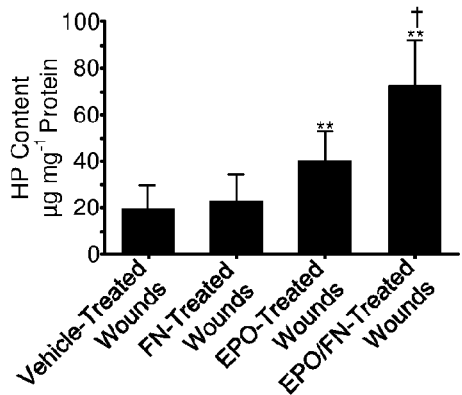
Figure 4D:
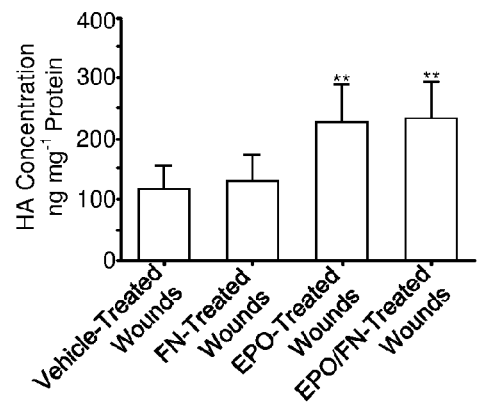
Figure 4E:
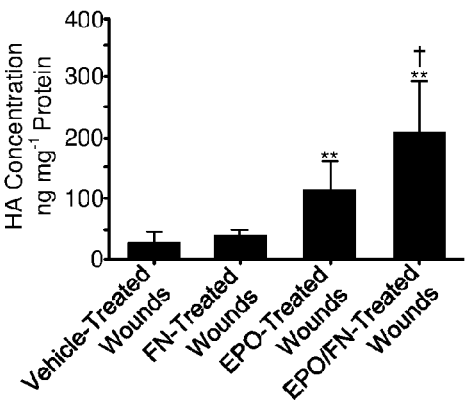
Figure 4F:
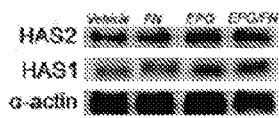
Figure 4G:
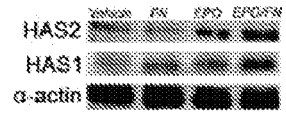

Topical EPO increases collagen deposition and hyaluronic acid (HA) synthesis in the regenerating skin of diabetic wounds and FN potentiates this effect. The amounts of hydroxyproline (HP) and HA and the expression levels of the two HA synthases, HAS1 and HAS2, in the vehicle-treated diabetic wounds were lower than those in the vehicle-treated non-diabetic wounds after 14 days (FIGS. 4A-G). Topical FN treatment for 14 days did not change the HP and HA amounts and the HAS1 and HAS2 expression levels in the diabetic and non-diabetic wounds (FIGS. 4B-G). On the other hand, topical EPO treatment for 14 days significantly increased the HP and HA amounts and the HAS1 and HAS2 expression levels in diabetic and non-diabetic wounds (FIGS. 4B-G). HP amounts in the EPO/FN-treated non-diabetic and diabetic wounds were significantly higher than those in the EPO-treated non-diabetic and diabetic wounds, respectively (FIGS. 4A-C). The HA amount and the HAS1 and HAS2 expression levels in the EPO/FN-treated non-diabetic wounds were very similar to those of the EPO-treated non-diabetic wounds (FIGS. 4D & 4F). In contrast, the HA amount and the HAS1 and HAS2 expression levels in the EPO/FN-treated diabetic wounds were significantly higher than those in the EPO-treated diabetic wounds (FIGS. 4E & 4G).

Figure 5A:
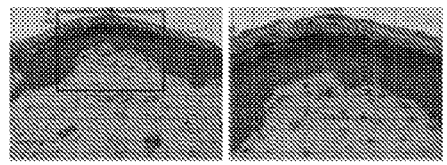
FIG. 5: AQP3 expression is decreased in wound-free diabetic skin. Representative set of micrographs of immunohistochemical staining for AQP3 in the wound-free skin of a non-diabetic pig (A) and a diabetic pig (B). Scale bars: (left) 50 μm; (right) 200 μm (A and B). (C) Representative set of micrographs of immunofluorescence staining for AQP3 in the wound-free skin of a non-diabetic pig and a diabetic pig (D). Scale bars: 200 μm (C and D). (E) Representative western blots of AQP3 expression in the wound-free skin of diabetic pigs 30 days after DM induction and wound-free skin of the non-diabetic pigs. Values are expressed as the mean ±standard deviation of triplicate determinations of AQP3 protein expression and as a percentage of the values in wound-free non-diabetic skin (100%). (G) α-Actin was used to normalize protein loading and the blots were derived from samples which were concomitantly run on a separate gel. (F) Total RNA was isolated from wound-free skin lysates that were prepared from samples of regenerating skin from the burn wound tissues of two diabetic and two non-diabetic pigs and were collected on day 14. AQP3 mRNA was quantified by RT-PCR. Values are expressed as the mean ±SD of triplicate measurements of AQP3 mRNA expression and as a percentage of the expression in wound-free of non-diabetic skin (100%). **$p<0.01$ and is the significance of the difference between healthy and diabetic pigs according to the results of a two-tailed Student's t test.
Figure 5B:
Figure 5C:
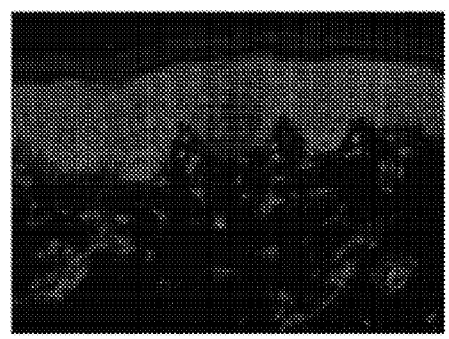
Figure 5D:
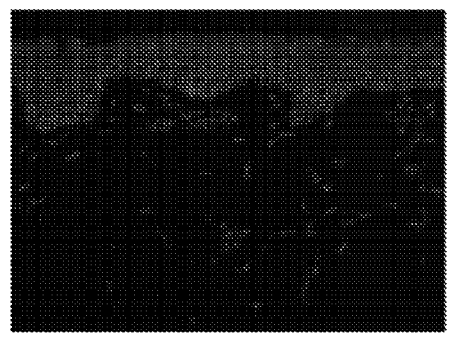
Figure 5E:
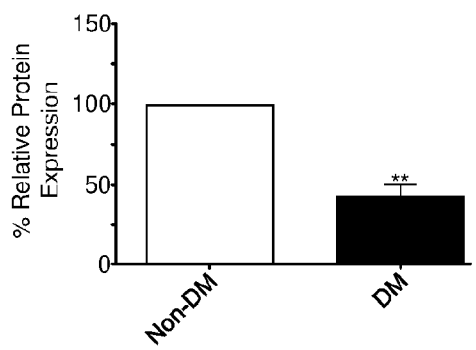
Figure 5F:
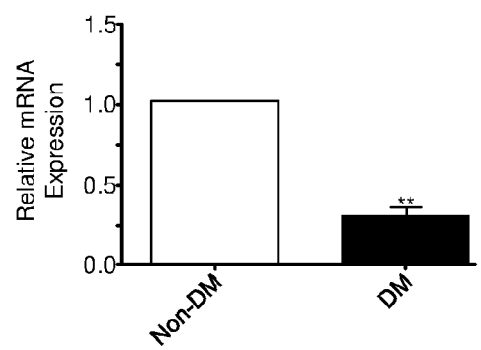
Figure 5G:
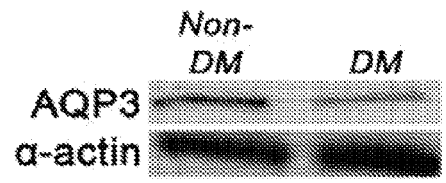
Figure 6A:
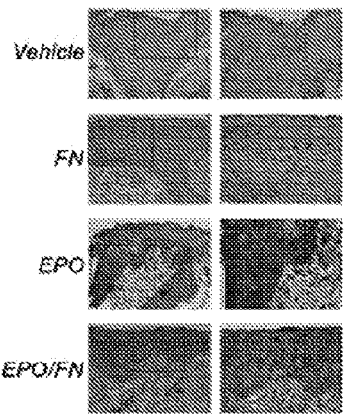
FIG. 6: Topical EPO stimulates AQP3 expression in the regenerating skin of diabetic wounds and this effect is potentiated by FN (A and B) Representative set of micrographs of immunohistochemical staining for AQP3 in the regenerating skin of the vehicle-treated, the FN-treated, the EPO-treated, and the EPO/FN-treated burn wounds of the non-diabetic pigs (A) and of the diabetic pigs (B) that were collected after 14 days of treatment. Scale bars: (A or B; left) 50 μm; (A or B; right) 200 μm. (C and D) Representative western blots of AQP3 protein expression after a 14-day treatment of burn wounds of two non-diabetic pigs (C) and two diabetic pigs with a vehicle-containing, an FN-containing, an EPO-containing, and an EPO/FN-containing gel Values are expressed as the mean ±SD of triplicate measurements of AQP3 protein expression in vehicle-treated burn wounds of the non-diabetic pigs (100%). Representative western blots of AQP3 protein expression in lysates of the regenerating skin of burn wounds from the non-diabetic pigs (E) and diabetic pigs (F) after 14 days of treatment α-Actin was used to normalize protein loading and the blots were derived from samples which were concomitantly run on a separate gel (G and H). Total RNA was isolated from lysates of the regenerating skin of vehicle-treated, FN-treated, EPO-treated, and EPO/FN-treated burn wounds of the non-diabetic pigs (G) and the diabetic pigs (H). AQP3 mRNA was quantified by RT-PCR. Values are expressed as the average ±SD of duplicate measurements of AQP3 mRNA expression AQP3 mRNA expression and as a percentage of the expression in wound-free of non-diabetic skin (100%). **$p<0.01$ and is the significance of the difference between the vehicle-treated burn wounds and the other treatments according to the results of a two-way ANOVA with Bonferroni's correction. †$p<0.05$ and is the significance of the difference between EPO/FN-treated burn wounds and the EPO-treated burn wounds according to the results of a two-tailed Student's t test.
Figure 6B:
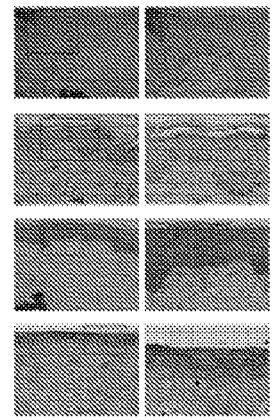
Figure 6C:
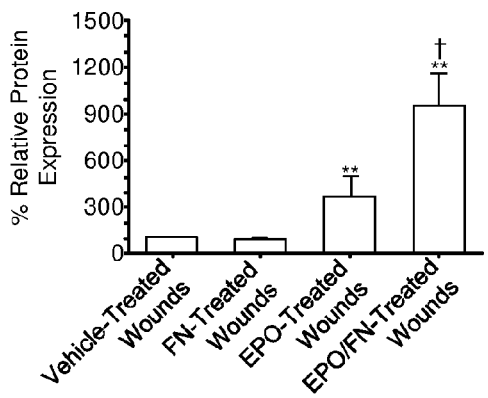
Figure 6D:
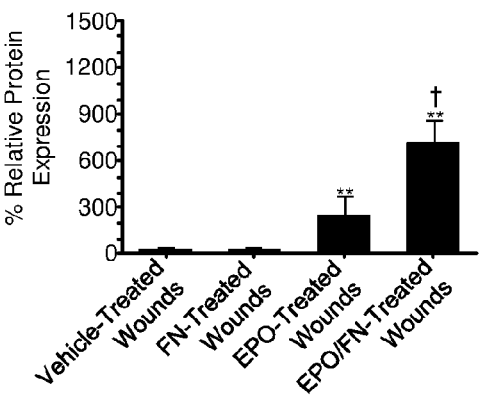
Figure 6E:
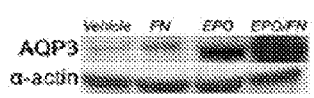
Figure 6F:
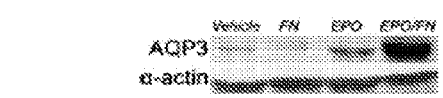
Figure 6G:
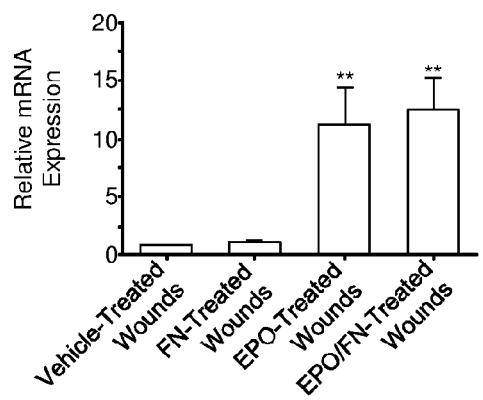
Figure 6H:
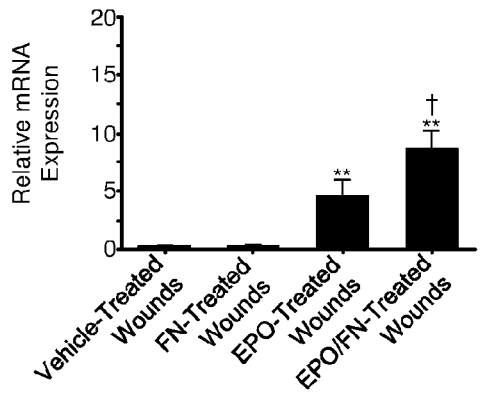

AQP3 expression is decreased in wound-free diabetic skin. AQP3 expression levels in wound-free diabetic pig skin were lower than those in the wound-free healthy pig skin (FIGS. 5A-D). AQP3 protein expression levels in wound-free diabetic pig skin were significantly lower ($p<0.01$) than those in wound-free healthy pig skin (FIG. 5E & 5G). This result is also reflected in AQP3 mRNA expression levels: AQP3 mRNA expression levels in wound-free diabetic skin were significantly lower ($p<0.01$) than those in wound-free healthy pig skin (FIG. 5F).

Topical EPO stimulates AQP3 expression in the regenerating skin of diabetic wounds and FN potentiates this effect After 14 days, AQP3 protein and mRNA expression levels in the vehicle-treated diabetic wounds were significantly lower than those in the vehicle-treated non-diabetic wounds (FIGS. 6A-H). In the diabetic and control pigs, AQP3 protein and mRNA expression in (a) the EPO-treated wounds were significantly higher than those of the vehicle-treated and FN-treated wounds, (b) the EPO/FN-treated wounds were significantly higher than that of the EPO-treated wounds, and (c) the vehicle-treated and FN-treated wounds were not different from each other (FIGS. 6A-6H).

AQP3 protein expression correlates positively with the extent of angiogenesis and HP and HA amounts in the regenerating skin of diabetic burn wounds. Pearson's correlation was used to investigate the relationships between AQP3 protein expression levels, the extent of angiogenesis, and the HP and HA amounts in the burn wounds of healthy and diabetic pigs. In the diabetic and healthy pigs, AQP3 protein expression levels correlated positively with the extent of angiogenesis (FIGS. 7A & 7B), the HP amount (FIGS. 7C & 7D), and the HA amount (FIGS. 7E & 7F). Interestingly, these correlations were significantly stronger in the regenerating skin of the burn wounds of the diabetic pigs than those found in the regenerating skin of the burn wounds of the healthy pigs.

AQP3 inhibition reduces the effect of topical EPO on the wound closure rate, the extent of angiogenesis, and the HP and HA amounts in diabetic burn wounds. When AQP3 activity was blocked by $HgCl_2$, the wound closure rates of $EPO/HgCl_2$-treated diabetic wounds days were significantly reduced (FIG. 8A). This reduction in wound closure rate was accompanied by a reduced blood flow (FIG. 8B), low eNOS expression levels (FIG. 8C), low HAS1 and HAS2 expression levels (FIG. 8C), a low extent of angiogenesis (FIG. 8D), a reduced HP amount (FIG. 8E), and a reduced HA amount (FIG. 8F). Moreover, the wound closure rates, the expression levels of eNOS, HAS1 and HAS2, and the amounts of HP and HA in the $EPO/HgCl_2$-treated diabetic wounds were significantly lower than those in the EPO-treated diabetic wounds.

High glucose downregulates AQP3 expression in keratinocytes and fibroblasts derived from human skin and this effect is blocked by EPO. The proliferation rate of HEKCs and NHFCs which were exposed to high glucose (HG) levels for five days was lower than that of cells that were exposed to normal glucose (NG) levels (FIGS. 9A & 9B). AQP3 expression levels in the HG-exposed cells were considerably lower than that in the NG-exposed cells (FIGS. 9C & 9D). EPO treatment restored normal AQP3 expression levels and the proliferation rate of the cells that were incubated in HG for five days.

Methods

Pig model of type 1 DM. The study comprised four 60 kg healthy female pigs (*Sus domesticus*), which were purchased from the Lahav Institute of Animal Research Institute (Kibbutz Lahav, Israel). Pigs were chosen as the experimental animal for this investigation because skin wound healing in pigs is similar to that of humans (Sullivan, 2001). The pigs were singly housed in pens in a room with an artificial 12-hour light/dark cycle at a constant temperature range (24±2° C.) and relative humidity (55±10%). The pigs were acclimated for one week prior to the study, and had free access to a standard laboratory chow and water. The maintenance and welfare of the pigs complied with (a) the guidelines on animal welfare and humane animal treatment that are delineated in the "Guide for the Care and Use of Laboratory Animals", $7^{th}$ edition, National Academies Press, Washington D.C., USA and (b) the Technion guidelines, which are in accordance with Israeli national legislation on the use of animals for experimental and other scientific purposes.

DM induction, creation of the burn wounds, wound treatment, dressing changes, and data collection were done under general anesthesia because it is very difficult to clean, treat, and bandage the wounds on conscious pigs without immobilization. General anesthesia was induced using intravenously administered propofol (5 mg/kg) and then maintained using 5% isoflurane in a 2:1 oxygen/nitrous oxide mixture after endotracheal intubation. An intravenous catheter was permanently placed in the right jugular vein under general anesthesia in the four pigs for blood sampling during the investigation and the infusion of fluids during DM induction in two pigs. Heart rate and blood oxygen saturation of the anesthetized pigs were monitored using non-invasive ear oximetry and the pig's body temperature was monitored using a digital rectal thermometer. After all procedures, the pigs were allowed to recover from anesthesia on the operating table, extubated, and then returned to their pens. On day 14, the last day of the experiment, the pigs were anesthetized for data and specimen collection and then humanely killed by an intravenous injection of KCl (2 mmol/kg; 40 ml) and an overdose of isoflurane (5%).

DM was induced in two pigs according to a previously described protocol (Hara, 2008). Briefly, the pigs were fasted overnight and were then hydrated with intravenous 0.9% NaCl (10 ml/kg/h) for one hour before administering streptozotocin (STZ; Alexis Biochemicals, San Diego, Calif., USA). STZ (200 mg/kg) was dissolved in 0.9% NaCl, and administered intravenously through the implanted intravenous cannula over one minute. Blood glucose levels were checked every 15 minutes for six hours after STZ administration using a glucometer (FreeStyle FREEDOM Lite, Abbot Diabetes Care Inc., Alameda, Calif., USA). Glucose (50 g dissolved in 100 ml water) was intravenously infused either continuously or intermittently during the first two hours after STZ administration in order to avoid severe hypoglycemia that may be caused by acute STZ-induced damage of the pancreatic β cells. Blood glucose levels were checked at least twice daily by a glucometer during the study period. DM induction was considered successful when the blood glucose levels were equal or higher than 300 mg/dl, six hours after STZ administration and persisted for the duration of the 14-day study period. Long-acting insulin (24 IU Lantus; Aventis Pharmaceuticals, Kansas City, Mo., USA) was injected intravenously to maintain the fasting blood glucose levels of the diabetic pigs between 300-400 mg/dl.

Creation of partial thickness skin burn wounds. DM was maintained for one month before partial thickness skin burn wounds were created under anesthesia. Once anesthetized, the bristles of the dorsal skin on each side of the vertebral column of each pig were removed using VEET depilatory cream (Reckitt Benckiser plc, Slough, Berkshire, UK). The skin was then cleaned with water and dried with tissues before creating 12-cm² circular partial thickness skin burn wounds on the clean dorsal skin of the pig using an aseptic technique. The burn wounds were created using a previously described method (Davis, 1990). Briefly, four cylindrical brass rods, each with a ~2.25-cm diameter and weighing 358 g, were placed in hot water (92° C.) for two minutes. Four groups of six partial thickness burn wounds were created by placing of the rod perpendicular on the dorsal skin of each anesthetized pig for 20 seconds with no additional pressure. In the two diabetic pigs, an additional group of six partial thickness burn wounds was created. Before applying the heated rod to the skin, the rod was wiped dry in order to prevent the creation of a steam burn on the skin from the evaporating water droplets.

EPO formulations for topical wound treatment. Six different gels for topical wound treatment were prepared in the Remedor Biomed laboratory in accordance with the recommendations in the United States Pharmacopoeia: (a) a gel which contained no active ingredients (vehicle gel), (b) a gel which contained 2000 IU/g EPO (high-dose EPO), (c) a gel which contained 500 IU/g EPO (low-dose EPO), (d) a gel which contained 300 µg/g FN, (e) a gel which contained 2000 IU/g EPO and 300 µg/g FN, and (f) a gel which contained 0.1 mM HgCl$_2$ and 2000 IU/g EPO. Recombinant human EPO was purchased as an injection (EPREX® 40,000 IU, Janssen Cilag Bucks, UK). FN was purchased as a 1 mg/ml solution (EMD Millipore, Billerica, Mass., USA). HgCl$_2$ (0.1 mM) was incorporated into the gel that contained 2000 IU/g EPO in order to block cutaneous AQP3 activity in the wounds (negative control) and was purchased from Sigma (Sigma-Aldrich, USA). The results of the stability testing of the gels established that EPO and FN are stable in the gel for at least three months at 4° C., as determined by ELISA.

| Formulation of Composition Used in Examples | | |
|---|---|---|
| Material name | %, w/w | Details (Vendor) |
| Erythropoietin (EPO) | 5 | JANSSEN-CILAG, EPREX 40000IU |
| Fibronectin (FN) | 30 | Probe International Inc |
| Glycerol | 5 | Merck |
| Carbomer 940 | 1 | Spectrum |
| Benzyl alcohol (BA) | 2 | Merck |
| Triethanolamine | ~0.9 | Merck |
| Methylparaben (MP) | 0.2 | Merck |
| Propylparaben (PP) | 0.05 | Merck |
| Water (WFI) | QS 100% | |
| Total | 100.0 | |

Preparation Method of Formulation. The formulation was prepared as follows:
1. The Methylparaben (MP) and Propylparaben (PP) were weighed into glass beaker and dissolved in Glicerol and Benzyl alcohol (BA).
2. ⅓ batch size of WFI was be added and stirred at 60° C. for 30 min. using heating plate and upper mixer.
3. Mixture is cooled with stirring to 30° C.
4. Add the required amount of Carbomer 940 slowly while stirring without heating.
5. Add EPO to the mixture and mix for 10 min
6. Add FN to the mixture and mix for 10 min.
7. Adjust pH to 6.5±0.3 by adding of sufficient amount of Triethanolamine.
8. Add sufficient amount of WFI to obtain the required weight.
9. Mix for 30 minutes at room temperature.

Preparation of a Preferred Batch of Topical Gel Carbopol 940 3000 IU/gr(grams) Erythropoietin (EPO) & 300 µg/gr (grams) Fibronectin (FN)

| Ingredients | For: 100 gr(grams) Batch size |
|---|---|
| EPO | *300000/BA |
| FN (1.0 mg/ml) | 30 gr(grams) |
| Benzyl Alcohol | 2 gr(grams) |
| Glycerin | 5 gr(grams) |
| Carbomer 940 p | 1 gr(grams) |
| Triethanolamine | qs ml(~0.9 gr(grams)) |
| Methylparaben | 200 mg |
| Propylparaben | 50 mg |
| water | qs 100 gr(grams) |

*According to biological activity results (From CoA or incoming testing)
BA = Biological activity (IU/ml)
Weight = 300000/X Method of preparation. The required quantity of each ingredient for total amount to be prepared. Each ingredient was accurately weighed. The total amount of Methylparaben and Propylparaben were mixed with the Glycerin and Benzyl Alcohol. About 40 grams of water was added to the mix and the mixture was mixed well for 30 min and up to 60° C. The Carbopol 940p was sprinkled slowly onto the rapidly agitated mixture and mix well at 30° C. All of the EPO to the mixture which was then mixed well for 10 min. The FN was then added to the mixture which was then mixed well for 10 min. Sufficient Triethanolamine was added to the mixture which was then mixed until the desired viscosity is obtained, after confirming there are no lumps of Carbopol 940p in the mixture. Sufficient water was added to an amount of total 100 gr(grams), and the mixture was mixed well. The gel was then packaged in Eppendorf vials of 1 gr(gram) each. The vials were then labeled with the batch No., preparation day and storage condition. A sample of 30 gr(grams) of the gel was taken for stability and microbiology tests and allocate as follows: a. 20 gr(grams) at 4 ° C. for Elisa tests b. 10 grams at 4 ° C. for microbiology tests.

Treatment of wounds with the various topical EPO formulations. Each group of the six partial thickness burn wounds was randomly assigned to be treated with one of the following topical gels: vehicle-containing gel, the high-dose EPO-containing gel, the FN-containing gel, and the EPO/FN-containing gel. The additional group of the burn wounds in one diabetic pig was treated with the EPO/$HgCl_2$-containing gel, and the additional group of burn wounds in the second diabetic pig was treated with low-dose EPO-containing gel (low-dose EPO) Gel (3 g) was topically applied to each wound every two days of the 14-day study period. In order to prevent removal of the gel after its application by rubbing and to protect the burn wounds between treatments, the treated wounds were covered with non-adherent gauze pads, which were stabilized by Tensoplast elastic adhesive bandaging (Smith & Nephew, London, UK). Post-operative analgesics and antibiotics were not administered because these drugs may influence the healing process, and thereby confound the interpretation of the data.

Study parameters. Each pig was weighed at the beginning and end of the 14-day study period, as well as during the study period. On each treatment day, each wound was photographed using a 12 megapixel digital camera (Olympus, Styles Tough, Tokyo, Japan), and a blood sample was collected for determining the red blood cell, leukocyte, and platelet counts, and the plasma hemoglobin and HbA1c levels. Punch biopsies from randomly selected areas of the regenerating skin of the vehicle-treated and treated burn wounds and the uninjured skin of the diabetic and non-diabetic pigs were collected on days 2, 7, and 14 using 6-mm circular blade. Samples of each biopsy specimen were fixed immediately in 10% neutral buffered formalin for histological determination of the MVD (see later for details) or stored in liquid nitrogen for the determination of protein levels using immunohistochemistry, western blot analysis, ELISA, and PCR (see later for details).

Determination of the wound closure rate. The wound closure rate was calculated from the area of reepithelialized tissue in the burn wound. In order to calculate the rate, the area of each burn wound was categorized into three areas (a) a scab area where the burnt skin becomes a rigid crust after creation of the burn injury, (b) a red area where the scab can be detached but has no epithelial cells, and (c) a white area where the scab can be detached and contains new epithelial cells. The wound closure rate was calculated by measuring the white area on days 2, 4, 7, 9, 11, and 14 when the wounds were treated and the bandage were replaced. To this end, transparent paper was placed over each wound, and the shape of the white area was drawn on the paper. The transparent paper was then superimposed onto a 1-mm² graph paper in order to measure the white area in the wound. The time-dependent changes in the size of the white rate were calculated using the following formula:

$$\% \text{ White area (wound closure)} = \frac{\text{White area on day } X}{\text{Wound area on day } 0} \times 100$$

All measurements of the white area were made by three examiners blinded to treatment modality.

Determination of blood flow in the burn wounds. Blood flow in the wounds was measured non-invasively by a laser Doppler perfusion imaging system (PeriScan PIM 2 System, Perimed, Stockholm, Sweden) at the beginning and the end of the 14-day study period and during the study period. Scanning of the wounds was done at the following settings: laser wavelength—670 nm (visible red), distance from the burn wounds—25 cm, scan resolution velocity—256×64 pixels, and scan duration—180 seconds. The scanner's probe was placed at a slight off-perpendicular angle to the skin in order to prevent reflection of laser beam from non-valid areas, as recommended in the device's manual. For each burn wound, a perfusion parameter, a laser Doppler perfusion index that scales linearly with tissue perfusion, was calculated from the reflection of laser beam from the moving erythrocytes. Perfusion in a region of interest (ROI) is measured on a scale of six colors in which dark blue depicts the lowest perfusion rate and red depicts the highest perfusion rate using the PIMSoft software for blood perfusion imaging (Lisca Development AB, Linkoping, Sweden). For each burn wound, the ROI was a 12-cm² circle that was drawn around the initial burn wound and the blood flow in the wound is the average value of all colors in the ROI.

Determination of the extent of angiogenesis in the regenerating skin of the burn wound tissues. CD31 is an adhesion molecule that is expressed by vascular endothelial cells and is widely used as a marker to demonstrate the presence of endothelial cells and newly-formed capillaries in tissues. This marker was used to determine the MVD and the extent of angiogenesis in the regenerating skin of the healing wounds. For this purpose, 5-μm thick sections of the formalin-maintained samples punch biopsies of the wounds, which were collected on days 2, 7, and 14, were prepared and mounted on glass slides for CD31 staining. Briefly, the specimens were embedded in paraffin blocks, deparaffinized using xylene, rehydrated in a series of graded propanol solutions (100-0%) in double deionized water ($ddH_2O$), and they were then immersed in Tris-buffered saline (TBS. pH 7.5) for five minutes. After treatment with TBS, endogenous peroxidase in the sections was blocked by immersing the slides in a 3% hydrogen peroxide/methanol solution for 20 minutes. The slides were then rinsed in phosphate buffered saline (PBS), and immersed in 10 mM citrate buffer solution (pH 6.0) at 90° C. for 10 minutes in order to unmask the antigen by microwave heating. The slides were first blocked with 1:50 normal goat serum (Sigma) for 30 minutes in order to eliminate non-specific staining by the antigen, rinsed in PBS, and then incubated overnight at 4° C. in the dark with 1:100 CD31 antibody (R&D Systems, MN, USA). After the overnight incubation, the slides were rinsed in PBS and counterstained with Mayer's hematoxylin (Sigma) for ten seconds before applying 1% acetic acid in order to differentiate the tissue section and rinsing under running tap water. The slides were examined under a Nikon Eclipse E800 upright microscope and images of the sections were captured and analyzed by Metamorph® image analysis software (Nikon Instruments Inc., Melville, NY, USA). The number of capillaries in the regenerating skin in each wound site was counted in five random microscopic fields (×200 magnification) by three investigators blinded as to treatment modality.

Detection of AQP3 in the regenerating skin of the burn wound tissues. AQP3 was detected in wound-free healthy and diabetic pig skin, one month after DM induction and one day before creation of the burn wounds, and in the regenerating skin of the wounds during the 14-day study period by immunohistochemistry and immunofluorescence. For AQP3 immunohistochemistry, 5-μm thick sections from specimens that were collected from the wound-free non-diabetic and diabetic pig skin and on day 2, 7, and 14 from the regenerating skin during the 14-day study period were prepared and mounted on glass slides in the identical manner that was described for CD31 staining. The sections were first blocked with 1:50 goat serum (Sigma) for 30 minutes, rinsed gently with PBS, and incubated overnight at 4° C. in the dark with 1:200 rabbit polyclonal AQP3 primary antibody (Santa Cruz Biotechnology, Santa Cruz, CA, USA). After the overnight incubation, the slides were rinsed in PBS and incubated with 1:400 biotinylated IgG secondary antibody (Vector Laboratories Inc., Burlingame, CA, USA) for 30 minutes at room temperature in the dark. After the incubation, the sections were washed gently with PBS and incubated with streptavidin peroxidase (Jackson ImmunoResearch, West Grove, PA) for 30 minutes at room temperature in the dark. Antigen detection was facilitated using an S-(2-aminoethyl)-1-cysteine (AEC/RED; Invitrogen Corp. Camarillo, CA, USA) as a substrate, until color signal development was observed. Slides were then rinsed immediately with PBS and counterstained with Mayer's hematoxylin solution (Sigma) for ten seconds before applying 1% acetic acid in PBS in order to differentiate the tissue sections. The sections were then rinsed in running tap water and, dehydrated in graded ethanol series for five minutes before they were mounted with Immu-Mount (Thermo Scientific, Pittsburgh, USA). Images of the sections were analyzed by Metamorph® image analysis software, as previously described.

For confirming AQP3 presence by immunofluorescence in the wound-free healthy and diabetic pig skin and in the regenerating skin of the wounds, another set of deparaffinized paraffin sections were incubated with 1:100 rabbit polyclonal AQP3 antibody (Santa Cruz) overnight at 4° C. After incubation, the slides were washed gently with tap water, incubated with 1:200 rhodamine-conjugated IgG secondary antibody (Jackson ImmunoResearch) for 30 minutes in the dark at room temperature, and then counterstained with the nuclear stain, TOPRO-3 (Invitrogen) for 30 minutes. At the end of the TOPRO-3 incubation, the slides were examined under a confocal microscope (Bio-Rad MRC 1024, CA, USA) after a gentle wash in PBS. Images of the sections were analyzed by Metamorph® image analysis software, as previously described.

Detection of collagen in the regenerating skin of the burn wound tissues. The amount of collagen in the regenerating skin was determined in specimens that were collected on days 2, 7, and 14 after Masson's trichrome staining (Sigma-Aldrich) of some of the 5-μm thick sections that were prepared for CD31 and AQP3 immunostaining. Using this method, collagen fibers stained blue, nuclei stained black, and cytoplasm and muscle fibers stained red. Images of the sections were analyzed by Metamorph® image analysis software, as previously described.

Determination of the amount of collagen in the regenerating skin of the burn wound tissues. Hydroxyproline (HP) is an amino acid constituent of type I collagen and is frequently used as a marker for collagen, Accordingly, the amount of HP in the skin specimens that were collected from the healthy and diabetic pigs on days 2, 7, and 14 were used as an indicator of the amount of collagen in the regenerating skin of the burn wounds. For this purpose, 100-mg skin samples were homogenized in PBS that contained complete protease inhibitor cocktail (Sigma-Aldrich, MO, USA) using a tissue homogenizer (HG-300; MRC, Holon, Israel). The homogenates were first centrifuged at 1500 g for five minutes at 4° C. The supernatant was collected, filtered through Whatman Grade 540 filter paper (Sigma-Aldrich), hydrolyzed in HCl, and then diluted with deionized water. Aliquots (2 μl) of the diluted solution were first mixed with a chloramine-T solution before adding p-dimethyl-aminobenzaldehyde, using a previously described protocol (Hamed, 2009). Aliquots (150 μl) of the resultant solution were then transferred to a microtiter plate, and the absorbance of each sample was measured in a fluorescent microplate reader at 557 nm. The results were expressed as the mean percentage of triplicate measurements of the amount of HP in the vehicle-treated burn wounds of the healthy pigs (100%).

Determination of the amount of HA in the regenerating skin of the burn wound tissues. Since HA is linked to skin strength and hydration, the HA amount in the regenerating skin of the burn wound tissues was determined in specimens that were collected from the non-diabetic and diabetic pigs on days 2, 7, and 14 using the Hyaluronan Quantikine ELISA Kit (R&D Systems) according to the manufacturer's protocol. Briefly, aliquots (150 μl) of the identical diluted solutions that were prepared for determining the HA amount in the regenerated skin of the burn wounds were transferred to a microtiter plate. The absorbance of each sample was then measured in a fluorescent microplate reader at 450 nm with wavelength correction set at 570 nm. The results were expressed as the mean percentage of triplicate measurements of the amount of HA in the vehicle-treated burn wounds of the healthy pigs (100%).

Determination of AQP3, eNOS, and HAS1, and HAS2 expression levels in the regenerating skin of the burn wound tissues by western blot analysis. Since AQP3 expression in regenerating skin is linked to skin hydration, the effect of EPO on AQP3 and cell hydration in the burn wound bed was investigated because AQP3 facilitates water entry to cells. Since HA is linked to skin strength and hydration, the effect of EPO on HAS1 and HAS2 expression was investigated because HA is a key molecule involved in skin moisture and is synthesized by HAS1 and HAS2. Since angiogenesis occurs in regenerating skin, the effect of EPO on eNOS expression was investigated because eNOS is the predominant NOS isoform in the vasculature and its expression level indicates the extent of angiogenesis. The expression levels of AQP3, eNOS, HAS1, and HAS2 were determined in the regenerating skin of the burn wound tissues that were collected from the healthy and diabetic pigs on day 14. Briefly, the samples were first homogenized in PBS that contained the Complete Protease Inhibitor Cocktail (Roche Applied Science) and then lysed in RIPA buffer. SDS-polyacrylamide gel electrophoresis was used to separate the proteins in 40-μg protein samples of the lysates. The separated proteins were then transferred to nitrocellulose membranes which were first incubated overnight in with a 1:100 polyclonal AQP3 antibody, a 1:150 monoclonal eNOS antibody, a 1:100 monoclonal HAS1 antibody, and a 1:100 monoclonal HAS2 antibody (all purchased from Santa Cruz Biotechnology, Santa Cruz, Calif., USA) in the dark at 4° C., and then incubated with a horseradish peroxidase (HRP)-conjugated IgG secondary antibody (Jackson ImmunoResearch. Europe) for 30 minutes at room temperature in the dark. α-Actin (Santa Cruz) was used to normalize protein loading. Protein expression levels were detected by densitometry using the Bio-Rad Immune-Star HRP chemiluminescence detection system (Bio-Rad, USA). The results were expressed as a percentage of the average protein level of duplicate readings in the vehicle-treated burn wounds of the healthy pigs (100%).

Real-time (RT) PCR for quantifying AQP3 mRNA levels. RT-PCR was used to investigate whether the effect of EPO on AQP3 expression is due to its effect on the AQP3 gene. Samples of regenerating skin from the burn wound tissues of diabetic and healthy pigs were collected on day 14 and homogenized in PBS. Total RNA was extracted from the homogenates using the MasterPure RNA purification kit (EPICENTER Biotechnologies, Madison, WI, USA). For each sample, approximately 2 μl of RNA, were reversed transcribed in triplicate using Absolute QPCR Mixes Reverse Transcription Reagents and the Verso cDNA Reverse Transcriptase kit, both of which were purchased from ABgene, UK. Quantification of AQP3 gene expression in the regenerating skin samples was done by RT-PCR using SYBR Green PCR Master Mix (Molecular Probes, Eugene, Oreg.) in a Rotor-Gene 6000 cycler (Corbett Life Science, Sydney, Australia). A standard curve-based method was used to assess PCR efficiency and intra-assay variation. The thermal cycling conditions were one cycle (10 min@95° C.), followed by 40 cycles (30 s@95° C., 1 min@60° C. and 30 s@72° C.), followed by one cycle (1 min@95° C., 30 s@55° C. and 30 s@95° C.). The $2^{-\Delta\Delta CT}$ method was used to analyze the relative changes in AQP3 gene expression in the treated, vehicle-treated, and untreated tissue samples that were collected from the non-diabetic and diabetic wounds. The results were expressed as a percentage change from control after normalization to an endogenous reference gene (glyceraldehyde-3-phosphate dehydrogenase; GAPDH).

Cell cultures. Primary human epidermal keratinocytes (HEKCs) and primary human fibroblasts (NHFCs), both of which were derived from neonatal foreskins (Cell Systems, Kirkland, WA, USA), express AQP3. The two cell types were individually propagated on type 1 collagen-coated flasks in CSC medium (Cell Systems) that was supplemented with 10% fetal bovine serum (FBS), 100 U/ml penicillin, 100 μg/ml streptomycin and 2 μg/ml amphotericin. Their ability to proliferate in the presence of NG concentrations (5 mmol/ml D-glucose) and HG concentrations (30 mmol/ml D-glucose) and EPO ((100 IU/ml) was determined because AQP3 is thought to be essential for their proliferation. For this purpose, the cells were first harvested, transferred to wells (~100,000 cells/well) of a type 1 collagen-coated 24-well plates that contained CSC medium with 10% FBS, and then exposed to HG concentrations with or without EPO (100 IU/ml) for five days in a humidified incubator which was set at 5% $CO_2$ and 37° C. After five days, proliferation of the HEKCs and NHFCs was measured using an MTT assay (Sigma) according to the manufacturer's protocol. Three replications of the assay were done and the results are expressed as the mean percentage±standard deviation (SD) of the proliferation rate of control non-treated cells (100%). Protein extracts of the two cell types were prepared in order to determine the AQP3 expression levels using western blot analysis, as previously described. An immunofluorescence assay was used to localize AQP3 in adherent HEKCs and NHFCs. For this purpose, cells were first fixed in 2% paraformaldehyde, and then incubated with a 1:100 rabbit polyclonal AQP3 antibody (Santa Cruz) at 4° C. for two hours. After incubation, the cells were washed gently in PBS before their incubation with 1:200 rhodamine-conjugated IgG secondary antibody (Jackson ImmunoResearch) for 30 minutes in the dark at room temperature. The nuclei of the cells were then counterstained with TOPRO-3 (Invitrogen) for 30 minutes. After counterstaining with TOPRO-3, the cells were washed gently in PBS and then examined under a confocal microscope (Bio-Rad MRC 1024, CA, USA). Images of the stained cells were analyzed by Metamorph® image analysis software, as previously described.

Statistics. All statistical analyses were done using a computerized statistical program (GraphPad Prism version 5.0, GraphPad Software Inc, CA, USA) and all data are presented as mean or percentage±SD. Statistical significance was set at 5%. A two-tailed Student's t test was used to compare study parameters of the healthy and diabetic pigs and a two-way ANOVA with Bonferroni's correction to control for type I error was used for multiple comparisons. Pearson's correlation coefficient was used to determine the relationships between AQP3 protein expression and (a) angiogenesis represented by MVD, (b) collagen content represented by the HP amount, and (c) the HA amount in the regenerating skin of the burn wound tissues. The wound closure rates among groups were compared and analyzed using a one-way ANOVA with Tukey's post-hoc test and a two-way ANOVA with Bonferroni's correction to control for type I error in the multiple comparisons. Data from the healthy and diabetic pigs were compared using a two-tailed Student's t test.

Discussion. The healing of a DSU is delayed because of impaired angiogenesis, reduced cutaneous cellular activity and increased inflammatory response. Consequently, chronic wounds develop, and in severe cases, limb loss may occur. Previously it has been reported that topical EPO accelerates the healing of full-thickness skin wounds of diabetic mice and rats through several mechanisms which include (a) stimulation of angiogenesis, (b) increased collagen deposition, (c) suppression of the inflammatory response, and (d) decreased cellular apoptosis in the wound bed (10, 11) (Hamed, 2010; 2011). A new mechanism has now been discovered by which topical EPO accelerates the healing of a diabetic skin wound: topically applied EPO increases AQP3 expression in the wound bed of healthy and diabetic pigs.

Raising AQP3 expression levels in the burn wounds of the diabetic pigs following topical EPO treatment reflects the net positive effect of EPO on angiogenesis and the HP and HA amounts and results in accelerated wound closure. Since the present inventor found that AQP3 expression is decreased in wound-free diabetic pig skin, it was postulated that low levels of cellular AQP3 underpin, at least in part, the non-healing of a DSU. Furthermore, it was also discovered that (a) AQP3 expression levels were lower in HG-treated keratinocytes and fibroblasts than those of NG-treated keratinocytes and fibroblasts and (b) the ability of HG-treated keratinocytes and fibroblasts to proliferate was less than those of NG-treated keratinocytes and fibroblasts. Interestingly, treatment with EPO could block this negative effect of HG on keratinocytes and fibroblasts. These findings imply that HG levels impair AQP3 expression in cutaneous cells, and provide in vitro corroboration for the inventors' experimental results in the skin of the pigs with DM. These are offered as possible explanatory mechanisms; the inventor is not intending to be bound by such theories.

It was found that AQP3 expression levels are associated with the wound closure rate in diabetic skin wounds. A growing body of evidence has suggested that an AQP3 deficiency in the regenerating skin of a DSU impairs epithelial cell migration and proliferation and results in decreased reepithelialization and delayed wound healing (Levin, 2006; Sigomoto, 2012). It has been reported that corneal epithelial cell migration, proliferation, and reepithelialization are stimulated by AQP3 (Levin, 2006). It has also been reported that downregulated expression of AQPs may be the cause of the reduction in urinary-concentrating ability in acute renal failure and that EPO can prevent this downregulation (Gong, 2004). Accordingly, it has been posited that stimulating local AQP3 expression in a DSU by EPO could accelerate wound healing. The results of this study provide evidence which supports the inventors' hypothesis that topical EPO treatment of burn injuries in the skin of diabetic pigs accelerated their healing through an AQP3-dependent mechanism by stimulating angiogenesis and ECM production. The results of this study also provide evidence that stimulating AQP3 expression in a non-healing ulcer by EPO further accelerates healing by increasing cell hydration and raising the wound's moisture levels. Increasing cell hydration and raising moisture levels facilitate interactions between the various cell types and ECM components. Such interactions results in proper cellular movement, migration, and differentiation, and ultimately restoration of intact skin.

Angiogenesis, synthesis of the ECM constituents such as collagen and HA, and proper cell hydration in the wound bed are indispensable for normal wound healing. EPO stimulates endothelial cell proliferation and the secretion of angiogenic cytokines and growth factors, such as vascular endothelial growth factor, fibroblast growth factor, and insulin-like growth factor-1 from endothelial cells and keratinocytes, to cause the sprouting of new blood vessels into the wound bed (Anagnostou, 1990). In this investigation, it was found that topical EPO treatment of a wound substantially increases blood flow in the regenerating skin of diabetic burn wounds as measured by laser Doppler scanning. This effect was confirmed when the MVD and eNOS expression levels in the regenerating skin of diabetic burn wounds were measured: the MVD and eNOS expression levels in the regenerating skin of EPO-treated diabetic burn wounds were higher than those in the regenerating skin of vehicle-treated diabetic burn wounds. Topical EPO treatment also resulted in significantly increased HP and HA amounts in the diabetic burn wounds. Vedrenne reported the existence of a close relationship between the ECM and the synthesis of molecules that regulate attachment between cells and the ECM, angiogenesis, skin wound healing, and turnover of resident dermal fibroblasts (Vedrenne, 2012). Cell hydration and a moist environment are critical for facilitating fibroblast turnover, angiogenesis, and reepithelialization by keratinocytes during wound healing. Therefore, any factor or event that prevents or limits local AQP3 protein expression and/or activation may reduce the level of cell hydration and impair wound healing. Collagen and HA have many functions in the ECM, of which one is to be a tissue scaffold for maintaining cellular shape and differentiation, supporting cellular movement and migration, and enabling the ECM in the dermal layer to resist compression.

HA is a very hydrophilic molecule and this property enables it to regulate tissue hydration because it attracts and binds water. It was found that AQP3 expression levels were reduced in the wound-free skin of the diabetic pigs. It was also discovered that, in addition to reduced angiogenesis and low HP and HA amounts, AQP3 expression levels in the regenerating skin of the vehicle-treated burn wounds in the diabetic pigs were lower than those in the regenerating skin of vehicle-treated burn wounds in the healthy pigs. It was also discovered that topical EPO treatment significantly increased angiogenesis and the HP and HA amounts in the diabetic wounds and that these increases were accompanied with a significant increase in AQP3 expression levels. It was also found that inhibition of AQP3 by $HgCl_2$ in the burn wounds of diabetic pigs antagonized the positive actions of EPO, and this result implies that EPO-mediated stimulation of AQP3 can stimulate wound healing in DM. Furthermore, it was also discovered that AQP3 expression levels were correlated with the extent of angiogenesis and the HP and HA amounts in the EPO-treated burn wounds of the healthy and diabetic pigs. It was also discovered that these correlations were stronger in the EPO-treated and EPO/FN-treated burn wounds of the diabetic pigs than those in the EPO-treated and EPO/FN-treated burn wounds of the healthy pigs. Since (a) EPO exerts a positive effect on AQP3 expression in the regenerating skin of wounds in diabetic pigs and (b) the correlations between AQP3 expression levels and the extent of angiogenesis and HP and HA amounts in the wound tissues before and after topical treatment are strong, it can be concluded that EPO-induced acceleration of healing is mediated through an AQP3-dependent mechanism(s). When this (these) mechanism(s) is (are) activated, the key events of the wound healing process, namely angiogenesis, collagen and HA synthesis, and reepithelialization, are stimulated and the wound closure rate is accelerated.

Reduced AQP3 expression in the regenerating skin during the healing of cutaneous full-thickness wounds of diabetic rats was reported by Sugimoto et al, 2012. Hara-Chikuma and Verkman also reported that the water content and elasticity of the stratum corneum are lower and that wound healing and ECM biosynthesis are slower in AQP3-knockout mice than in wild-type mice (Hara-Chikuma, 2008a). Interestingly, AQP3 expression in human skin is increased in some skin diseases, such as atopic eczema and skin carcinomas (Hara-Chikuma, 2008b), and cutaneous burn wounds (Sebastian, 2015). These findings imply that AQP3 is a key player in epidermal biology, skin restoration after an injury is boosted when AQP3 is stimulated.

It was furthermore discovered that the slow wound closure rate of the diabetic wounds is associated with reduced angiogenesis and low HP and HA amounts in the wound bed. It was also discovered that the reduced ability of HG-treated HEKCs and NHBCs to proliferate is associated with reduced AQP3 expression levels in the cells. These findings imply that reduced AQP3 expression levels are due to HG concentrations and underlie the reduced proliferation of keratinocytes and fibroblasts in DM. Since It was also discovered that the adverse effects of HG concentrations on cell proliferation and AQP3 expression are prevented by EPO, the evidence suggests that EPO accelerates the healing of diabetic wounds through an AQP3-dependent mechanism(s) that spare(s) the tissue of some of the effects of HG concentrations.

Another interesting finding was that AQP3 expression levels in the EPO/FN-treated diabetic wounds were four times higher than those in the EPO-treated diabetic wounds. This substantial increase in AQP3 expression levels in the EPO/FN-treated diabetic wounds is associated with rapid wound closure rates and elevated blood flow and a two-fold increase in the MVD and the HP and HA amounts in the wound tissues. FN and fibrin are two critical constituents of the provisional matrix that supports macrophages, fibroblasts, and angiogenesis (Stadelmann, 1998). Proper formation of the provisional matrix and granulation tissue enables reepithelialization and wound closure (Martin, 1997). In DM, a deficiency in FN and/or its degradation by proteases leads to disintegration of the provisional matrix and reepithelialization does not occur or is delayed. It has been previously reported that the healing of topically EPO/FN-treated cutaneous wounds of diabetic mice is faster than that of topically EPO-treated cutaneous wounds of diabetic mice (Hamed, 2011). FN has an essential function in the formation of granulation tissue during the proliferative phase of wound healing. Hence, the inventor posited that exogenous FN can restore the normal provisional matrix in diabetic wounds. It was discovered that FN alone has no effect on wound closure rate, the blood flow rate, the extent of angiogenesis, and the HP and HA amounts in burn wounds of healthy pigs. It was furthermore discovered that exogenous FN does not potentiate the accelerating action of EPO on the healing of burn wounds of healthy pigs because endogenous FN is present in normal levels and not degraded in healthy pigs. Since endogenous FN is degraded in a DSU, incorporating FN in to an EPO-containing gel is desirable because FN potentiates the salutary actions of an EPO-containing gel.

The inventor has thus demonstrated that topical EPO application to a diabetic wound accelerates reepithelialization and the wound closure rate, thus it is surmised based on the findings in a diabetic pigs that the application of topical EPO may be therapeutically beneficial for stimulating the healing of a DSU by raising cutaneous AQP3 expression levels.

Example 2

Treatment of Chronic Diabetic Ulcers in Humans

The formula of Example 1 was tested to determine effectiveness for treating chronic diabetic ulcers in a human patient. A 77 year old male patient diagnosed with diabetes mellitus, hypertension and hyperlipidemia presented with a diabetic ulcer on his dorsal, medial right foot. The lesion was approximately 9.6 $cm^2$ (See FIG. 13, "BEFORE" panel).

Patient Parameters

| | |
|---|---|
| Gender: | Male |
| Age: | 77 years old |
| Ethnicity: | North African |
| Smoking: | No smoking history |
| Medical history: | diabetes mellitus, hypertension, hyperlipidemia |
| Height: | 176 cm |
| Weight: | 96 kg |
| BMI: | 30.99 kg · m−2 |
| ABI | 0.76 (Mild Obstruction) |
| Hemoglobin | 12.3 g/dL |
| HCT | 36.5% |
| RBC | 4.13 10^8/µl |
| Platelets Count | 169 10^3/µl |
| Glucose | 159 mg/dL |
| Concomitant Medication (ongoing): | |
| Amlodipine | since 2015 |
| Metformin | since 2015 |
| Pravastatin | since 2013 |
| Cartia | since 2002 |
| Enaladex | since 2012 |

Diabetic Foot Ulcer
Location: dorsal, medial position
Area: 9.6 $cm^2$
History: more than 2 months with no improvement
Wagner type: I
Aerobic bacteria (*Pseudomonas aeruginosa*)

The wound was gently debrided prior to application of the composition on day 1. The composition of Example 1 was topically applied to the wound five days a week at a dosage of 0.25 $g/cm^2$ of the wound, according to the area of the ulcer on the day of treatment. Treatment lasted for almost eight weeks (55 days) and included 36 topical applications of the composition of Example 1 until the complete closure of the wound, as was diagnosed by a physician. The treatment was provided at patient's home by a visiting nurse. The patient visited the outpatient department weekly for ulcer assessment, tests, and evaluations. FIG. 13 ("AFTER" panel) is a photo of the completely closed wound after the 8-week treatment.

The treatment with the composition of Example 1 over eight weeks did not have any noticed systemic effect, i.e. did not cause significant changes in blood parameters or blood pressure. Some of the parameters are presented below in the Table 3.

TABLE 3

| Measured parameter | Before the treatment | After the treatment |
|---|---|---|
| Hemoglobin (g/dL) | 12.3 | 12.5 |
| HCT (%) | 36.5 | 37.8 |
| RBC (10^8/µl) | 4.13 | 4.32 |
| Platelets Count (10^3/µl) | 169 | 167 |
| Blood pressure (mmHg) | 139/70 | 139/79 |

Adverse Effects

Hyper-granulation was observed after three weeks of treatment. It was considered as a minor adverse effect. Due to it the treatment was paused for 3 days, while three daily drug applications were skipped. After three days interval the hyper-granulation effect decreased and the treatment was continued. No further signs of hyper-granulation were observed until the end of the treatment course.

Conclusion

The treatment of patient K. by RMD-G1 was safe and efficient. A complete closure of the chronic diabetic wound was observed within eight weeks of treatment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Agre, et al. "The aquaporins, blueprints for cellular plumbing systems." J Biol Chem. 1998; 12;273(24):14659-62.

Anagnostou, et al., "Erythropoietin has a mitogenic and positive chemotactic effect on endothelial cells." Proc Natl Acad Sci USA. 1990 Aug; 87(15):5978-82.

Brown, et al., "Expression of vascular permeability factor (vascular endothelial growth factor) by epidermal keratinocytes during wound healing." J Exp Med. 1992; 176:1375-9

Davis, et al., "Second-degree burn healing: the effect of occlusive dressings and a cream." J Surg Res. 1990 Mar; 48(3):245-8.

Gong, et al., "EPO and alpha-MSH prevent ischemia/reperfusion-induced down-regulation of AQPs and sodium transporters in rat kidney." Kidney Int. 2004; 66:683-695.

Hamed, et al., "Topical erythropoietin promotes wound repair in diabetic rats." J Invest Dermatol 2010; 130: 287-94.

Hamed, et al., "Fibronectin potentiates topical erythropoietin-induced wound repair in diabetic mice." J Invest Dermatol 2011; 6: 1365-74.

Hamed, et al., "Erythropoietin, a novel repurposed drug: An innovative treatment for wound healing in patients with diabetes mellitus." Wound Repair Regen. 2014 Jan-Feb; 22(1):23-33.

Hara, et al., "Safe induction of diabetes by high-dose streptozotocin in pigs." Pancreas. 2008 Jan; 36(1):31-8. doi: 10.1097/mpa.0b013e3181452886.

Hara-Chikuma & Verkman, "Aquaporin-3 functions as a glycerol transporter in mammalian skin." Biol Cel 2005; 97:479-86.

Hara-Chikuma & Verkman, "Physiological roles of glycerol-transporting aquaporins: the aquaglyceroporins." Cell Mol Life Sci. 2006; 63(12):1386-92.

Hara-Chikuma & Verkman, "Aquaporin-3 facilitates epidermal cell migration and proliferation during wound healing." J Mol Med. 2008; 86:221-31

Hara-Chikuma & Verkman, "Roles of aquaporin-3 in the epidermis." J Invest Dermatol. 2008; 128:2145-51

Hehenberger, et al., "Impaired proliferation and increased L-lactate production of dermal fibroblasts in the GK-rat, a spontaneous model of non-insulin dependent diabetes mellitus." Wound Repair Regen 1999, 7:65-71

Levin & Verkman, "Aquaporin-3-dependent cell migration and proliferation during corneal re-epithelialization." Invest Ophthalmol Vis Sci. 2006; 47(10):4365-72.

Mansbridge, et al., "Growth factors secreted by fibroblasts: role in healing diabetic foot ulcers." Diabetes Obes Metab 1999, 1:265-79

Martin, "Wound healing—aiming for perfect skin regeneration." Science 1997; 276:75-81.

Mustoe, "Understanding chronic wounds: a unifying hypothesis on their pathogenesis and implications for therapy." Am J Surg 2004, 187:65S-70S Sebastian, et al., "Epidermal aquaporin-3 is increased in the cutaneous burn wound." Burns. 2015 Jan. 17.

Sen, et al., "Human skin wounds: a major and snowballing threat to public health and the economy." Wound Repair Regen 2009; 17: 763-71.

Sheetz & King, "Molecular understanding of hyperglycemia's adverse effects for diabetic complications." JAMA 2002, 288:2579-88

Shukla, et al., "Differential expression of proteins during healing of cutaneous wounds in experimental normal and chronic models." Biochem Biophys Res Commun. 1998; 244:434-9

Stadelmann, et al., "Physiology and healing dynamics of chronic cutaneous wounds." Am J Surg. 1998; 176:26S-38S Sugimoto, et al., "Impaired Aquaporin 3 Expression in Reepithelialization of Cutaneous Wound Healing in the Diabetic Rat." Biol Res Nurs. 2012; 15(3): 347-55.

Sullivan, et al., "The pig as a model for human wound healing." Wound Repair Regen. 2001; 9(2):66-76.

Tentolouris, et al., "Moisture status of the skin of the feet assessed by the visual test neuropad correlates with foot ulceration in diabetes." Diabetes Care. 2010; 33(5):1112-4.

Vedrenne, et al., "The complex dialogue between (myo) fibroblasts and the extracellular matrix during skin repair processes and ageing." Pathol Biol (Paris). 2012; Feb; 60(1):20-7.

Winter, "Formation of the scab and the rate of epithelialization of superficial wounds in the skin of the young domestic pig." Nature.1962; 20;193:293-4.

The invention claimed is:

1. A method of treating a wound in a subject comprising administering to the subject a therapeutically effective amount of a composition that induces aquaporin expression; wherein the composition comprises an erythropoietin protein at a concentration of between 0.01% to 30% (w/w),
fibronectin protein at a concentration of between 0.01% to 50% (w/w),
glycerol at 5% (w/w),
Carbomer 940 at 1% (w/w),
benzyl alcohol at 2% (w/w),
triethanolamine at about 0.9% (w/w),
methylparaben at 0.2% (w/w),
propylparaben at 0.05% (w/w), and
water to 100% (w/w).

2. The method of claim 1, wherein the erythropoietin protein is present at a concentration of 5% (w/w).

3. The method of claim 1, wherein the composition comprises:
5% (w/w) erythropoietin protein; and
wherein the composition is a gel.

4. The method of claim 1, wherein the composition consists of:
5% (w/w) erythropoietin protein; and
30% (w/w) fibronectin protein;
5% (w/w) glycerol;
1% (w/w) Carbomer 940;
2% (w/w) benzyl alcohol;
0.9% (w/w) triethanolamine;
0.2% (w/w) methylparaben;
0.05% (w/w) propylparaben; and
water to 100% (w/w);
wherein the composition is a gel.

5. The method of claim 1, wherein the composition is a gel.

* * * * *